(12) United States Patent
Shestakov

(10) Patent No.: US 7,744,926 B2
(45) Date of Patent: Jun. 29, 2010

(54) USE OF A BIOLOGICALLY ACTIVE BLOOD SERUM FOR THE TREATMENT OF STROKE

(75) Inventor: Vitali A. Shestakov, Moscow (RU)

(73) Assignee: Owen Holding Ltd., Isle of Man (GB)

( * ) Notice: Subject to any disclaimer, the term of this patent is extended or adjusted under 35 U.S.C. 154(b) by 319 days.

(21) Appl. No.: 11/404,971

(22) Filed: Apr. 14, 2006

(65) Prior Publication Data
US 2006/0257496 A1      Nov. 16, 2006

Related U.S. Application Data

(60) Provisional application No. 60/672,269, filed on Apr. 18, 2005.

(51) Int. Cl.
*A61K 35/16*    (2006.01)
*A61K 35/14*    (2006.01)
*A61K 35/12*    (2006.01)

(52) U.S. Cl. .................. 424/531; 424/520; 424/529

(58) Field of Classification Search .................. None
See application file for complete search history.

(56) References Cited

FOREIGN PATENT DOCUMENTS

EP       1 283 047 A        2/2003
WO     WO 2005/058889 A     6/2005

OTHER PUBLICATIONS

Wang R-Y et al. 2001. Protective effects of treadmill training on infarction in rats. Brain Res 922: 140-143.*
Gabis L et al. 2003. Immediate influence of transcranial electrostimulation on pain and beta-endorphin blood levels. Am J Phys Med Rehabil 82: 81-85.*

* cited by examiner

*Primary Examiner*—Lora E Barnhart
(74) *Attorney, Agent, or Firm*—Saliwanchik, Lloyd Saliwanchik

(57) ABSTRACT

The present invention relates to the use of a pharmacologically active blood serum product producible by a method comprising electrostimulation of a non-human animal, withdrawal of blood from said animal, isolation of serum from said blood, and gamma irradiation of said serum in the treatment of stroke, preferably ischemic stroke.

26 Claims, 13 Drawing Sheets

USE OF A BIOLOGICALLY ACTIVE BLOOD SERUM FOR THE TREATMENT OF STROKE

CROSS-REFERENCE TO A RELATED APPLICATION

Figure 1:
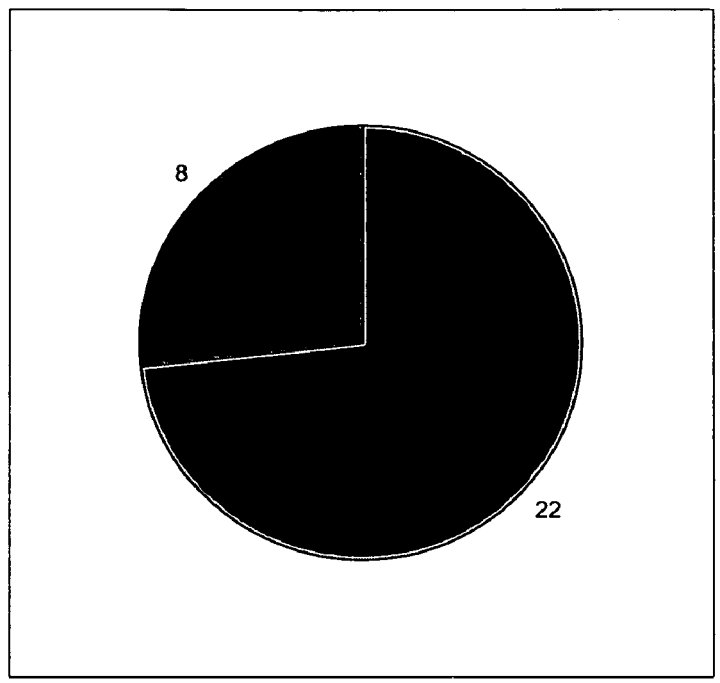
Figure 1:
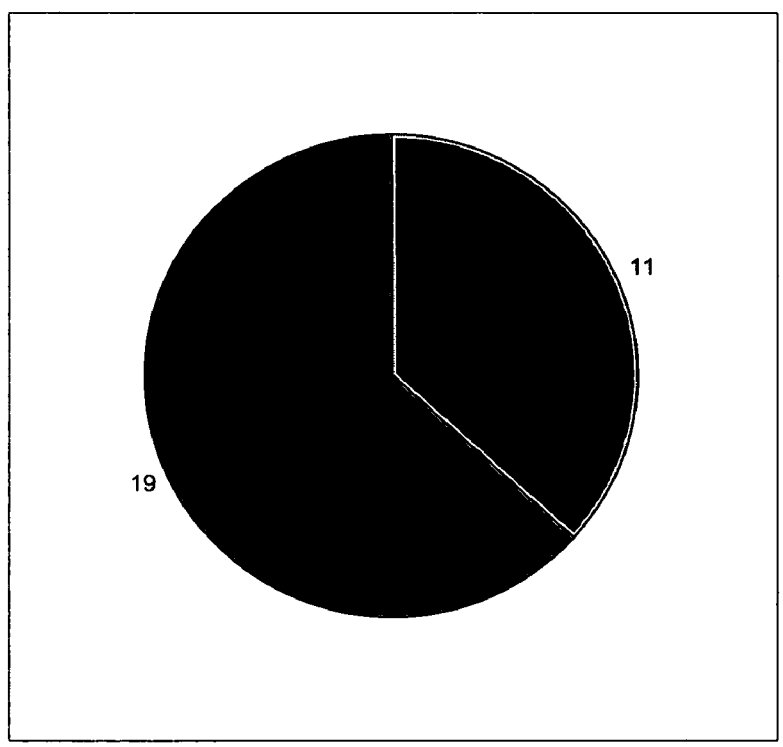

This application claims the benefit of U.S. provisional application Ser. No. 60/672,269, filed Apr. 18, 2005.

The present invention relates to the use of a pharmacologically active blood serum product producible by a method comprising electrostimulation of a non-human animal, withdrawal of blood from said animal, isolation of serum from said blood, and gamma irradiation of said serum in the treatment of stroke, in particular ischemic stroke.

BACKGROUND OF THE INVENTION

Stroke is a debilitating disease which affects more than 400,000 persons per year in the United States alone. At current trends, this number is projected to jump to one million per year by the year 2050. When the direct costs (care and treatment) and the indirect costs (lost productivity) of strokes are considered together, strokes put a burden of $43.3 billion per year on the society of the United States alone. In 1990 cerebrovascular diseases were the second leading cause of death worldwide, killing over 4.3 million people world wide. Stroke is characterized by the sudden loss of circulation to an area of the brain, resulting in a corresponding loss of neurologic function. Also called cerebrovascular accident or stroke syndrome, stroke is a nonspecific term encompassing a heterogeneous group of pathophysiologic causes, including thrombosis, embolism, and hemorrhage. Strokes currently are classified as either hemorrhagic or ischemic. Acute ischemic stroke refers to strokes caused by thrombosis or embolism and account for 80% of all strokes.

Ischemic strokes result from blockage of the arteries that supply the brain, most commonly in the branches of the internal carotid arteries. The blockage usually results when a piece of a blood clot (thrombus) or of a fatty deposit (atheroma) due to atherosclerosis breaks off (becoming an embolus), travels through the bloodstream, and lodges in an artery that supplies the brain. Blood clots may form when a fatty deposit in the wall of an artery ruptures. The rupture of such a fatty deposit may also form when a large fatty deposit slows blood flow, reducing it to a trickle. Blood that flows slowly is more likely to clot. Thus, the risk of a clot forming in and blocking a narrowed artery is high. Blood clots may also form in other areas, such as in the heart or on a heart valve. Strokes due to such blood clots are most common among people who have recently had heart surgery and people who have a heart valve disorder or an abnormal heart rhythm (arrhythmia), especially atrial fibrillation. Also, in certain disorders such as an excess of red blood cells (polycythemia), the risk of blood clots is increased because the blood is thickened.

An ischemic stroke can also result, if the blood flow to the brain is reduced, as may occur when a person loses a lot of blood or has very low blood pressure. Occasionally, an ischemic stroke occurs when blood flow to the brain is normal but the blood does not contain enough oxygen. Disorders that reduce the oxygen content of blood include severe anemia (a deficiency of red blood cells), suffocation, and carbon monoxide poisoning. Usually, brain damage in such cases is widespread (diffuse), and coma results. An ischemic stroke can occur, if inflammation or infection narrows blood vessels that supply the brain. Similarly, drugs such as cocaine and amphetamines can cause spasm of the arteries, which can lead to a narrowing of the arteries supplying the brain to such an extent that a stroke is caused.

Most ischemic strokes begin suddenly, develop rapidly, and cause death of brain tissue within minutes to hours. Then most strokes become stable, causing little or no further damage. (Strokes that remain stable for 2 to 3 days are called completed strokes.) Such strokes are more likely to be due to sudden blockage by an embolus. Less commonly, strokes may continue to worsen for several hours to a day or two, as a steadily enlarging area of brain tissue dies. (Such strokes are called evolving strokes.) The progression is usually interrupted by somewhat stable periods, during which the area temporarily stops enlarging or some improvement occurs. Such strokes are more likely to be due to formation of clots in a narrowed artery.

Many different symptoms can occur, depending on which part of the brain is deprived of blood and oxygen. When the arteries that branch from the internal carotid artery are affected, blindness in one eye or abnormal sensations and weakness in one arm or leg or on one side of the body are most common. When the arteries that branch from the vertebral arteries in the back of the brain are affected, dizziness and vertigo, double vision, and generalized weakness of both sides of the body are more common. Many other symptoms, such as difficulty speaking (for example, slurred speech) and loss of coordination, can occur. Large strokes may lead to stupor or coma. In addition, strokes, even small ones, can cause depression or an inability to control emotions (causing inappropriate crying or laughing). Strokes can cause swelling in the brain due to accumulation of fluid (edema). Swelling in the brain is particularly dangerous because the skull does not expand. The resulting increase in pressure can cause the brain to shift and damage brain tissue further, making neurologic dysfunction worse, even if the area affected by the stroke itself does not enlarge. If the pressure becomes very high, the brain may even be forced downward in the skull, resulting in herniation of the brain.

In the past, almost nothing could be done to help patients with acute stroke. Recently advances have been made in stroke prevention, supportive care, and rehabilitation. For an evolving stroke, anticoagulants such as heparin may be given, but their effectiveness has not been proved. After the stroke is completed, anticoagulants are given to prevent subsequent strokes in people who have atrial fibrillation or a heart valve disorder. However, because these drugs increase the risk of bleeding into the brain, doctors usually wait at least 24 hours after thrombolytic therapy is ended before anticoagulants are started. Anticoagulants are not given to people who have uncontrolled high blood pressure or who have had a hemorrhagic stroke. Accordingly, there is still a large need in the art to develop novel therapeutic compounds capable of preventing, treating or ameliorating the severe health consequences of stroke including death.

SUMMARY OF THE INVENTION

It has been surprisingly found by the present inventor that a biological active blood serum was capable to reduce the debilitating effects of stroke, in a relevant animal model of stroke. Accordingly, the present invention provides a novel approach for treating and preventing stroke, in particular ischemic stroke. Thus, in one embodiment the present invention is concerned with the use of a biological active blood serum producible according to a method comprising the steps of:

a) electrostimulation of a non-human animal
b) withdrawal of blood from said animal,
c) isolation of serum from said blood, and
d) gamma irradiation of said serum for the prevention and treatment of stroke, in particular of ischemic stroke.

Preferably, the non-human animal is selected form the group consisting of mammals and birds, preferably from poultry, e.g. chicken, duck, turkey, goose, ostrich, and quail. Preferred mammals are rodents, house and farm animals, preferably mice, hamsters, rats, dogs, cats, sheep, cows, horses, donkeys, pigs, goats, and apes.

Although the electrostimulation can be employed to any part of the body it is preferred that step a) of the method to produce a biologically active blood serum for the use of the present invention is applied to the head, the neck, the body and/or one or more limbs of the animal. Out of those preferred areas it is particularly preferred that the head of the respective animal is electrostimulated.

In a preferred embodiment of the use of the present invention the electrostimulation is carried out for a time period of between 1 and 60 seconds, preferably between 1 and 30 seconds, and more preferably between 2 and 10 seconds. It is also preferred that the electrostimulation is carried out with a voltage in the range of between 50 V and 150 V, preferably in the range of between 80 V to 120 V, and more preferably in the range of between 110 V and 120 V. During the performance of the electrostimulation certain currents are preferred and preferably the electrostimulation is carried out with a current in the range of between 0.01 A and 0.4 A, preferably in the range of between 0.02 A and 0.1 A, and more preferably in the range of between 0.04 A and 0.06 A.

In a preferred embodiment of the use of the present invention the electrostimulation is carried out with a frequency in the range of between 10 and 200 Hz, preferably in the range of between 20 to 100 Hz and more preferably in the range of between 45 to 65 Hz.

In a further preferred embodiment of the use of the present invention the gamma irradiation is administered with an adsorbed radiation dose of between 10 to 40 kGy, preferably 15 to 35 kGy and more preferably of between 20 and 30 kGy. Preferably this dose is administered for a time period of 30 min to 10 h, preferably 45 min to 8 h and more preferably 1 to 5 h. The gamma radiation source can be any source, however, a preferred source of gamma radiation is selected from the group consisting of $^{60}Co$, $^{137}Cs$, $^{67}Cu$, $^{67}Ga$, $^{111}In$, $^{192}Ir$, $^{99m}Tc$ and $^{170}Tm$. Preferably the radiation source is $^{60}Co$.

In a further preferred embodiment of the use of the present invention the method for producing the biological active blood serum further comprises the step of incubating said blood prior to step c).

In a further preferred embodiment of the use of the present invention the method for producing the biological active blood serum further comprises the step of lyophilization of said serum prior to step d).

In a preferred embodiment of the use of the present invention the blood drawn or harvested from the animal is arterial and/or venous blood.

In a preferred embodiment of the use of the present invention the biologically active blood serum further comprises one or more pharmaceutically acceptable diluents; carriers; excipients, including fillers, binders, lubricants, glidants, disintegrants, adsorbents; and/or preservatives.

In a preferred embodiment of the use of the present invention the biologically active blood serum is formulated as a syrup, an infusion or injection solution, a tablet, a capsule, a capslet, lozenge, a liposome, a suppository, a plaster, a band-aid, a retard capsule, a powder, or a slow release formulation. Preferably the diluent is water, a buffer, a buffered salt solution or a salt solution and the carrier preferably is selected from the group consisting of cocoa butter and vitebesole.

In a further preferred embodiment of the use of the present invention the biologically active blood serum is administered to a subject in need of curative or prophylactic treatment in an amount ranging from 0.1 to 200 mg/kg body weight, preferably ranging from 50 to 150 mg/kg body weight and more preferably from 90 to 100 mg/kg body weight.

In a further preferred embodiment of the use of the present invention the biologically active blood serum is administered prior to or within 24 hours after a stroke.

In a further preferred embodiment of the use of the present invention the administration is continued for at least 1 week after the stroke.

In a further preferred embodiment of the use of the present invention said stroke is selected from an ischemic, thrombotic, embolic, or transient stroke.

DETAILED DESCRIPTION OF THE INVENTION

The present inventor has surprisingly found that a biologically active blood serum can be isolated from non-human animals upon the stimulation of animals, in particular of chickens with electric currents and further treatment of the serum with γ-radiation which can then be used for the prophylaxis and treatment of stroke, in particular of ischemic stroke.

Methods for the preparation of substances with some pharmacological activity from blood serum are known in the art. One is based on the withdrawal of blood from humans or animals, the subsequent incubation as well as the separation of the active substance and finally the preservation of the substance (see, for example, JP 2123287, EP 0 542 303, RU 2096041, RU 2120301). The prior art method concerned the preparation of a blood serum which improves the resistance of the body in respect of exogenic and endogenic factors like air pressure, air temperature, gravity, light etc. as well as hunger, thirst, sleeping and sexual desires etc. The blood serum is drawn from the donor who has previously been brought into a certain functional state and according to the length of the application of the functional state and the type of functional state, e.g. sleep deprivation, alcohol abuse, nicotine abuse etc., blood serum with different biological activity can be obtained which shows mitogenic, somnogenic, opthalmogenic, audio active, thermo active, dietary active, sexually active, anti-hypoxic, anti-alcohol and anti-nicotine activity.

A different method is disclosed in EP 1 283 047 and concerns the treatment of animal blood serum by gamma irradiation with the aim to increase the biological activity of the blood serum product.

Earlier experiments have shown that stimulation of animals with electricity leads to an increase of the β-endorphin level in the blood (see, for example, Litvinova S. V. et al. (1990) *Biomed. Sci.* 5: 471). In a reference work by Udovitschenko, W. I. numerous data is provided with respect to the results of stimulation or shock due to various causes. It has been shown that, for example, electroshock leads to a marked increase of the concentration of β-endorphines, meta- and leu-encephalines within the blood (see Udowitschenko, W. I. (1989) "Xenogenic Opioid System in Shock" *Pathiological Physiology and Experimental Therapy*" 6: 72-77).

In none of these studies it was suggested that a biologically active blood serum let alone a biologically active blood serum produced by initially electrostimulating a non-human animal and subsequently by treatment with γ-irradiation would have the ability to prevent and treat, e.g. ameliorate the debilitating effects of stroke.

Accordingly, a first aspect of the present invention is the use of a biologically active blood serum producible by a method comprising the steps of:
a) electrostimulation of a non-human animal,
b) withdrawal of blood from said animal,
c) isolation of serum from said blood, and
d) gamma irradiation of said serum for the production of a therapeutic for the prevention and/or treatment of stroke, in particular ischemic stroke.

Various non-human animals can be used in the production of the biologically active blood serum, however, it is preferred that the non-human animal is selected from the group consisting of mammals and birds. Because of their easy availability it is particularly preferred to use farm animals like poultry, e.g. chicken, duck, turkey, goose, ostrich and quail. A particular preferred animal which can be used in the method of the present invention is a chicken. The type of mammal that can be used in the method of the present invention is not particularly restricted and comprises without limitation rodents and farm animals, e.g. mice, hamsters, rats, cats, dogs, horses, donkeys, sheep, cows, pigs and goats.

Without wishing to be bound by any theory, it is envisioned by the present inventor that the electrostimulation leads to the release of certain compounds within the animal which cause and/or contribute to the surprising effect of the biological active blood serum of the present invention on stroke. The non-human animal can be stimulated in different regions of the body. Preferably the electrostimulation is carried out at the head, the neck, the body and/or on one or more of the limbs. It is possible to stimulate the body only at one position or at several positions at once. A particular preferred body part for the electrostimulation is the head of the respective animal. When stimulating birds, in particular chicken it is preferred that the head is electrostimulated. In the context of the present invention the terms electrostimulation and electroshock are used interchangeably.

The electrostimulation can be carried out by art known methods, preferably using metal electrodes or water baths as used, for example, during culling of cattle or electrocution of poultry. Preferably, the electrostimulation is carried out for a time period of between 1 and 60 seconds, preferably between 1 and 30 seconds, more preferably between 2 and 10 seconds, and most preferably between 3 and 4 seconds. The length of the time period of electro stimulation will usually be longer in case that a large animal is electrostimulated and will usually be shorter in cases were small animals are electrostimulated. For example, for the stimulation of chicken heads a particular preferred time period of the electrostimulation is between 2 and 10 seconds and more preferably between 3 and 4 seconds. The other variables which can be adapted during the electrostimulation of the animal is the voltage, the current and the frequency of the current and the present inventors have defined certain preferred ranges for these parameters. The actual parameter chosen will depend in part on the size of the animal as well as on the region of the animal to be stimulated. In general larger animals and larger regions will require a higher voltage and current. Thus, the electro stimulation is preferably carried out with a voltage in the range of between 50 Volt and 150 Volt, preferably 80 Volt to 120 Volt and more preferably between 110 Volt and 120 Volt. The ranges for the currents that can be applied are between 0.01 A and 0.4 A, preferably between 0.02 A and 0.1 A, more preferably between 0.04 A and 0.06 A and most preferably about 0.05 A. Voltage, current and application time are preferably chosen to administer energy in the range of between 1 and 1,000 Ws, preferably in the range of 10 to 200 Ws and even more preferably in the range of 15 to 100 Ws.

For the stimulation of the preferred animals, i.e. chicken, it is preferred that the electrostimulation is carried out with a voltage in the range of between 80 Volt to 120 Volt and more preferably between 110 Volt and 120 Volt. Furthermore, a current in the range of between 0.04 A and 0.06 A, in particular of 0.05 A is preferred in the context of the electrostimulation of birds, in particular of chicken. Preferably, the electrostimulation of a bird, in particular a chicken, is carried out for between 3 and 4 seconds at a voltage of between 80 V and 120 V, in particular 110 V and 120 V. In this preferred embodiment the current is preferably between 0.04 A and 0.06 And most preferably about 0.05 A.

The frequency of the electrostimulation does not appear to be particularly critical but is preferably in the range of between 10 and 200 Hertz, more preferably in the range of between 45 to 65 Hz and most preferably around 50 Hz.

The gamma irradiation of the serum during step d) of the method of producing the biologically active blood serum can be carried out with any gamma source including X-ray sources and radionuclides. Preferably the gamma irradiation source is a radionuclide with a defined gamma irradiation pattern. Preferred sources for the gamma irradiation are selected from the group consisting of $^{60}$Co, $^{137}$Cs, $^{67}$Cu, $^{67}$Ca, $^{111}$In, $^{192}$Ir, $^{99m}$Tc and $^{170}$Tm. Out of those $^{60}$Co, $^{137}$CS, $^{192}$Ir and $^{170}$Tm are particular preferred with $^{60}$Co being the most preferred gamma radiation source for use in the method of the present invention.

The radiation dose adsorbed by the serum is preferably in the range of between 10 to 40 kGy preferably in the range of between 15 to 35 kGy and more preferably in the range of between 20 and 30 kGy, i.e. 25±5 kGy. Gamma irradiation on one hand sterilizes the serum and the other bolsters the activity of the serum. The suitable irradiation time can vary in a wide range, depending on the desired level of activity of the resulting serum and the respective indication for which the serum is to be used. The experimental section describes assays to test the activity of the serum of the invention and these tests can be used by someone of skill in the art to determine the optimal duration of the application of irradiation without an undue burden. Preferably the irradiation is carried out for a period of time in the range of 30 min to 10 hours, preferably for 45 min to 8 h and more preferably for 1 h to 5 h, i.e. for 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295 or 300 min. It is further preferred that the energy dose applied for this period of time is within a range of 10 to 40 kGy, preferably 15 to 35 kGy and more preferably between about 20 to 30 kGy. Again the preferred radiation source in this context is $^{60}$Co.

The withdrawal of the blood from the animal can be affected by any art known method and includes syringes as well as puncturing of arteries or veins or decapitation in particular in the context of the withdrawal of blood from birds. It is possible to withdraw only a part of the blood or to completely withdraw the blood of the animal. The later is preferably used, if a lethal dose of electricity has been applied to the animal. The withdrawn blood can be arterial and/or venous blood.

The serum can be isolated from the blood by any known method including filtration, sedimentation and centrifugation. It is, however, preferred that the blood is incubated for between 4 and 72 h at a low temperature, e.g. between 2° C. and 10° C., preferably between 4 and 8° C. to allow clotting of the blood which leads to the release of additional factors into the blood. Thus, it is preferred that the method of producing the biologically active blood serum further comprises the step of incubating the blood after the withdrawal of the blood from the animal and prior to the isolation of the serum from the blood, e.g. for between 4 and 72 h at a low temperature, e.g. between 2° and 10° C., preferably between 4° C. and 8° C.

In a further preferred embodiment of the use of the present invention the method for producing the biologically active blood serum comprises the further step of lyophilization of the serum prior to the irradiation step d). The lyophilization allows easier handling of the serum during irradiation and optimizes absorption of the radiation by the serum components.

In a further embodiment of the use of the present invention the biological active blood serum is formulated to further comprise one or more pharmaceutically acceptable diluents; carriers; excipients, including fillers, binders, lubricants, glidants, disintegrants, and adsorbents; and/or preservatives.

The biological active blood serum can be administered by various well known routes, including oral, rectal, intragastrical and parenteral administration, e.g. intravenous, intramuscular, intranasal, intradermal, subcutaneous and similar administration routes. Parenteral administration and particular intravenous administration is preferred. Depending on the route of administration different pharmaceutical formulations are required and some of those may require that protective coatings are applied to the drug formulation to prevent degradation of the biological active serum in, for example, the digestive tract.

Thus, preferably the biological active blood serum is formulated as a syrup, an infusion or injection solution, a tablet, a capsule, a capslet, lozenge, a liposome, a suppository, a plaster, a band-aid, a retard capsule, a powder, or a slow release formulation. Preferably the diluent is water, a buffer, a buffered salt solution or a salt solution and the carrier preferably is selected from the group consisting of cocoa butter and vitebesole.

Particular preferred pharmaceutical forms for the administration of the biological active blood serum during the use of the present invention are forms suitable for injectionable use and include sterile aqueous solutions or dispersions and sterile powders for the extemporaneous preparation of sterile injectable solutions or dispersion. In all cases the final solution or dispersion form must be sterile and fluid. Typically, such a solution or dispersion will include a solvent or dispersion medium, containing, for example, water-buffered aqueous solutions, e.g. biocompatible buffers, ethanol, polyol, such as glycerol, propylene glycol, polyethylene glycol, suitable mixtures thereof, surfactants or vegetable oils. The biological active blood serum used in the present invention can also be formulated into liposomes, in particular for parenteral administration. Liposomes provide the advantage of increased half life in the circulation, if compared to the free drug and a prolonged more even release of the enclosed drug.

Sterilization of infusion or injection solutions can be accomplished by any number of art recognized techniques including but not limited to addition of preservatives like anti-bacterial or anti-fungal agents, e.g. parabene, chlorobutanol, phenol, sorbic acid or thimerosal. Further, isotonic agents, such as sugars or salts, in particular sodium chloride may be incorporated in infusion or injection solutions.

Production of sterile injectable solutions containing the biological active blood serum is accomplished by incorporating the biological active serum in the required amount in the appropriate solvent with various ingredients enumerated above as required followed by sterilization. To obtain a sterile powder the above solutions are vacuum-dried or freeze-dried as necessary. Preferred diluents of the present invention are water, physiological acceptable buffers, physiological acceptable buffer salt solutions or salt solutions. Preferred carriers are cocoa butter and vitebesole. Excipients which can be used with the various pharmaceutical forms of the biological active blood serum can be chosen from the following non-limiting list:

a) binders such as lactose, mannitol, crystalline sorbitol, dibasic phosphates, calcium phosphates, sugars, microcrystalline cellulose, carboxymethyl cellulose, hydroxyethyl cellulose, polyvinyl pyrrolidone and the like;

b) lubricants such as magnesium stearate, talc, calcium stearate, zinc stearate, stearic acid, hydrogenated vegetable oil, leucine, glycerids and sodium stearyl fumarates, c) disintegrants such as starches, croscaramellose, sodium methyl cellulose, agar, bentonite, alginic acid, carboxymethyl cellulose, polyvinyl pyrrolidone and the like.

Other suitable excipients can be found in the Handbook of Pharmaceutical Excipients, published by the American Pharmaceutical Association, which is herein incorporated by reference.

Based on the results in animals certain amounts of the biological active blood serum are preferred for the prevention or treatment of stroke. It is, however, understood that depending on the severity of the stroke and the particular type, e.g. ischemic, thrombotic, embolic, or transient stroke, as well as on the respective patient to be treated, e.g. the general health status of the patient, etc., different doses of the biological active blood serum or the pharmaceutical composition are required to elicit a therapeutic or prophylactic effect. The determination of the appropriate dose lies within the discretion of the attending physician. It is contemplated that the dosage of the biologically active blood serum in the therapeutic or prophylactic use of the invention should be in the range of about 0.1 mg to about 1 g serum per kg body weight. However, in a preferred use of the present invention the biologically active blood serum is administered to a subject in need thereof in an amount ranging from 1.0 to 500 mg/kg body weight, preferably ranging from 10 to 200 mg/kg body weight, preferably ranging from 50 to 150 mg/kg body weight, preferably ranging from 90 to 100 mg/kg body weight. The duration of therapy with biologically active blood serum will vary, depending on the severity of the disease being treated and the condition and idiosyncratic response of each individual patient.

As is known in the art, the pharmaceutically effective amount of a given composition will also depend on the administration route. In general the required amount will be higher, if the administration is through the gastrointestinal tract; e.g. by suppository, rectal, or by an intragastric probe, and lower if the route of administration is parenteral, e.g. intravenous. Typically, the biologically active blood serum will be administered in ranges of 50 mg to 1 g/kg body weight, preferably 100 mg to 500 mg/kg body weight, if rectal or intragastric administration is used and in ranges of 10 to 100 mg/kg body weight, if parenteral administration is used.

If a person is know to be at risk of developing a stroke a prophylactic administration of the biologically active blood serum is possible. In these cases the biologically active blood serum is preferably administered in above outlined preferred and particular preferred doses on a daily basis. Preferably, between 0.1 mg to 1 g/kg body weight once a day, preferably 10 to 200 mg/kg body weight. This administration can be continued until the risk of developing a stroke has lessened. In most instances, however, the biologically active blood serum will be administered once a stroke has been diagnosed. In these cases it is preferred that a first dose of the biologically active blood serum is administered for the first time within 24 hours after a stroke. Preferably the administration is then continued for preferably at least 7, more preferably at least 14 and more preferably for at least 21 days. The doses are administered preferably once a day and preferably in above indicated doses.

It is further preferred that the stroke is selected from an ischemic, thrombotic, embolic, or transient stroke.

The following examples are included to demonstrate preferred embodiments of the invention. It should be appreciated by those of skill in the art that the techniques disclosed in the examples that follow represent techniques discovered by the inventors to function well in the practice of the invention, and thus, can be considered preferred modes for its practise. However, those of skill in the art should, in light of the present disclosure, appreciate that many changes can be made in the specific embodiments that are disclosed without departing from the spirit and scope of the invention as set out in the appended claims. All references cited are incorporated herein by reference.

BRIEF DESCRIPTION OF THE FIGURES AND DRAWINGS

FIG. 1: Pie charts of morbidity after the experimentally induced ischemic stroke. The upper panel depicts the number of deceased rats in the group "stroke+physiologic solution" while the lower panel depicts the deceased rats in the group "stroke+serum". The dark grey areas depict the deceased animals, while the light grey area depicts the surviving animals in the respective treatment groups.

Figure 2:
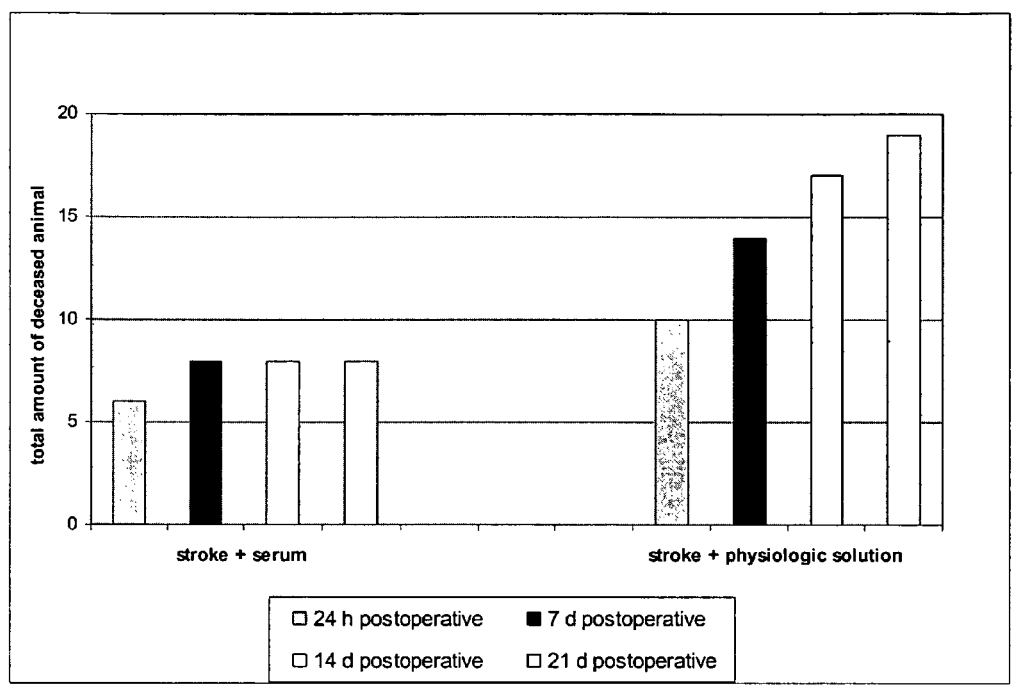

FIG. 2: Bar graphs of the number of death of rats in the different treatment groups. Total amount of the deceased rats in the respective groups shown at different points after time induction of stroke with or without the administration of the biological active serum of the present invention.

Figure 3:
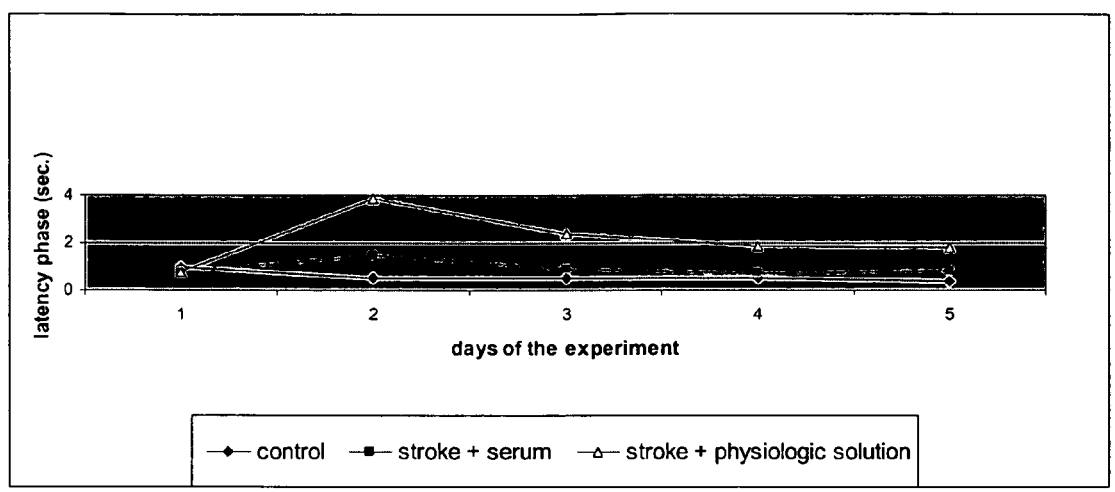

FIG. 3: Dynamic of the latency phase for leaving the middle for rats of the various groups in the "open field" test. This graph depicts the latency phase of the rats placed in the middle of an open field for control animals and animals treated with either serum or physiologic solution after induction of an experimental stroke. Day 1 of the experiment is immediately prior to the induction of the stroke, day 2 of the experiment is 24 h post operative, day 3 of the experiment is 7 days post operative, day 4 of the experiment is 14 days post operative and day 5 of the experiment is 21 days post operative.

Figure 4:
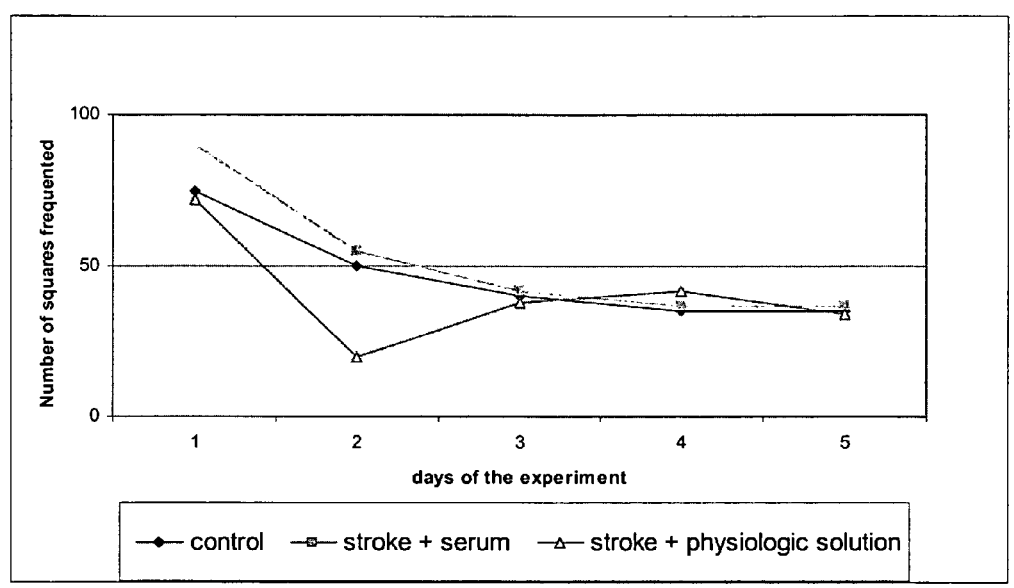

FIG. 4: Dynamic of the squares frequented in the "open field" test. This graph depicts the number of squares, which are drawn on the surface of the open field, and which were entered by the rats once released in the open field. The days of experiment have the meaning as in FIG. 3

Figure 5:
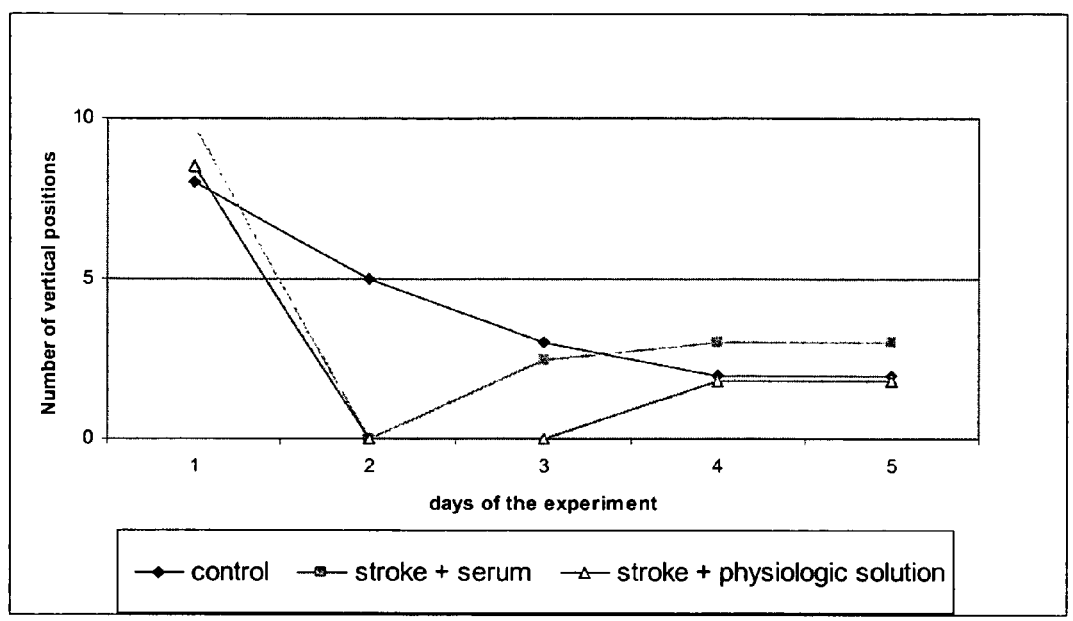

FIG. 5: Dynamic of the vertical activity in the "open field" test. This graph depicts the number of times that the rats upright themselves within a given time period. The days of experiment have the meaning as in FIG. 3

Figure 6:
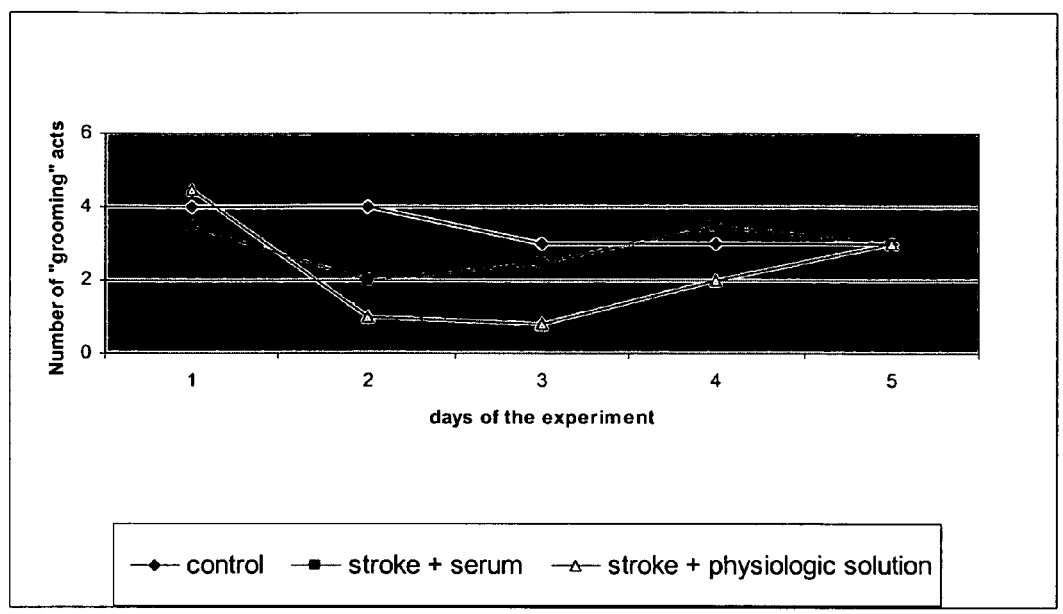

FIG. 6: Dynamic of the stereotype activity in the "open field" test. The stereotype activity scored in this test is the number of "grooming" action performed by control rats or rats with an induced stroke which had been treated with either serum or physiologic solution. The days of experiment have the meaning as in FIG. 3

Figure 7:
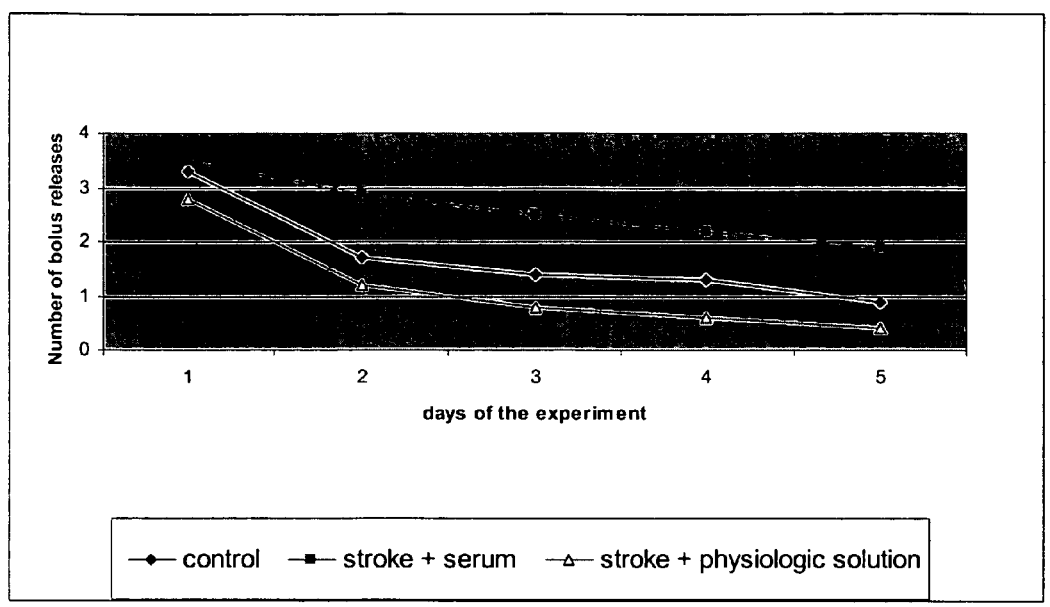

FIG. 7: Dynamic of bolus release in the "open field" test. The graph depicts the number of bolus releases during the performance of the experiment at different days of the experiment with control rats as well as with rats with an experimental induced stroke treated with either serum or physiologic solution. The days of experiment have the meaning as in FIG. 3

Figure 8:
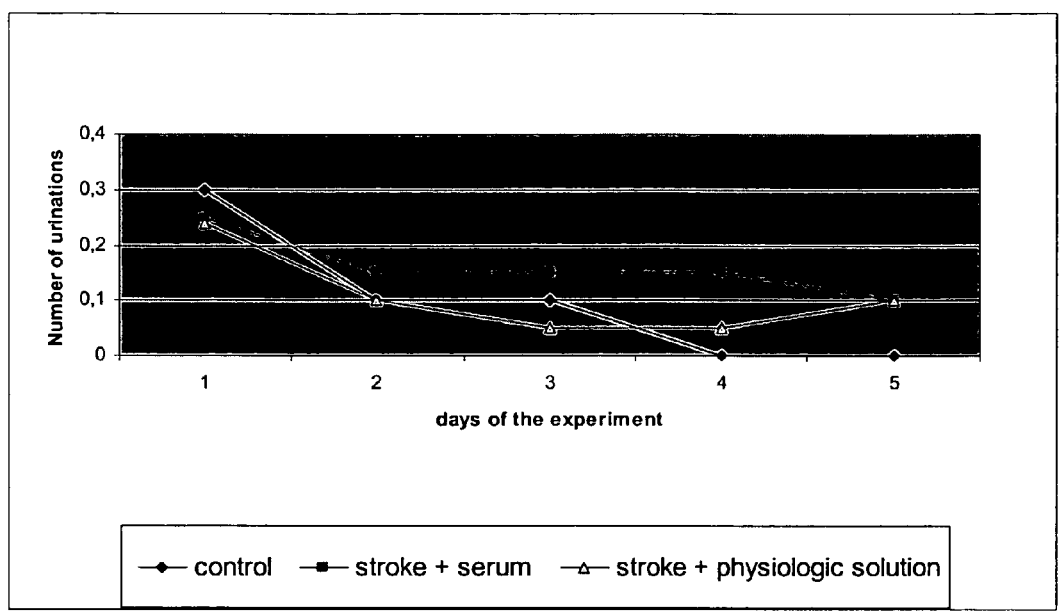

FIG. 8: Dynamic of urinating in the "open field" test. The graph depicts the number of times control rats or rats with an induced stroke treated with either serum or a physiologic solution urinated in the "open field" test on different days of the experiment. The days of experiment have the meaning as in FIG. 3

Figure 9:
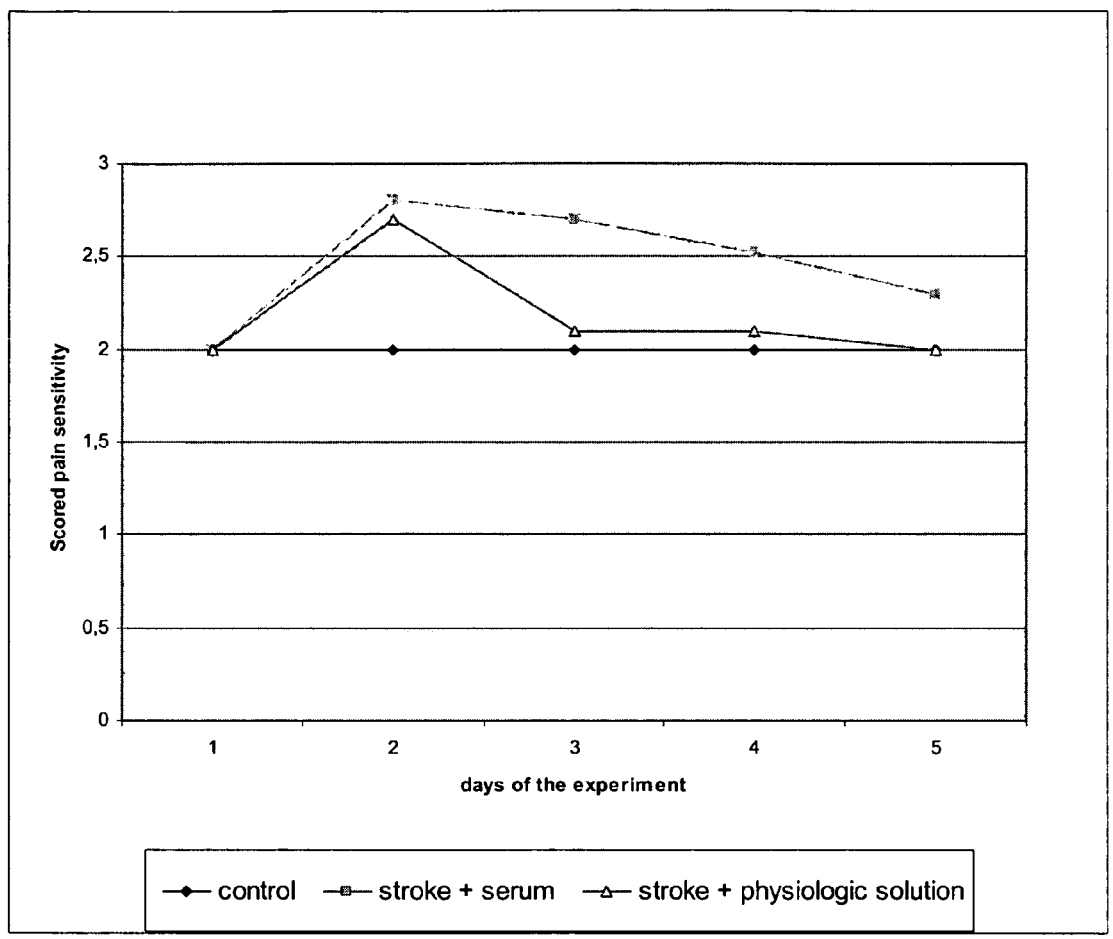

FIG. 9: Dynamic of the pain sensitivity in the "hot plate" test for rats of the various groups. The graph depicts the scored pain sensitivity of control rats or rats with an induced stroke and treated with either serum or a physiologic solution at different days of the experiment. The days of experiment have the meaning as in FIG. 3

Figure 10:
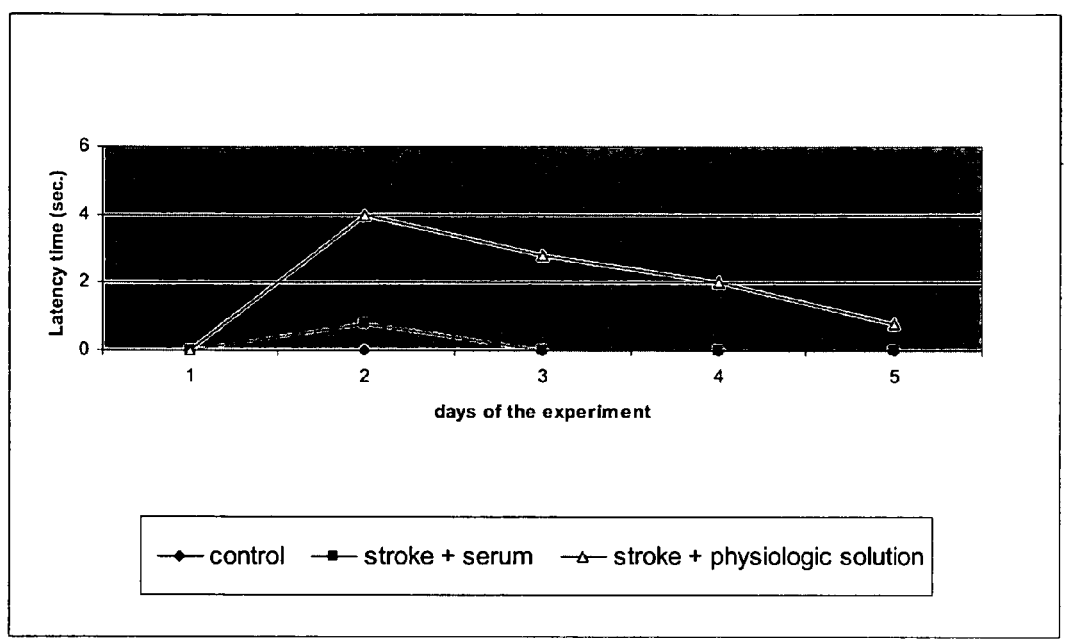

FIG. 10: Dynamic of the latency phase of turning around in the lateral position test in the various groups. The graph depicts the latency phase of the "righting reflex" from lateral position of control rats and rats with an induced stroke treated with either serum or a physiologic solution at different days of the experiment. The days of experiment have the meaning as in FIG. 3

Figure 11:
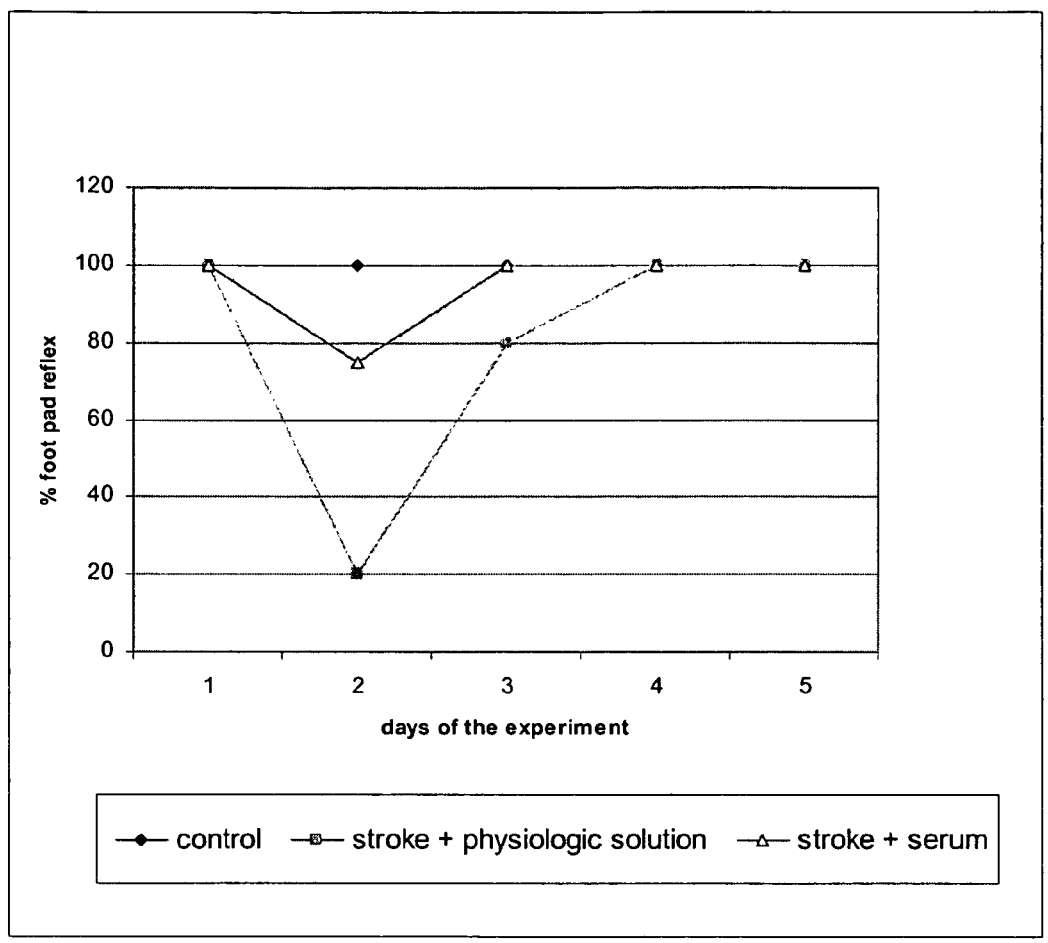

FIG. 11: Dynamic of the foot pad reflex in the various groups. The graph depicts the foot pad reflex of control rats and rats with an induced stroke treated with either serum or physiologic solution at different days of the experiment. Foot pad reflex of the control group is arbitrarily set to 100%. The days of experiment have the meaning as in FIG. 3

Figure 12:
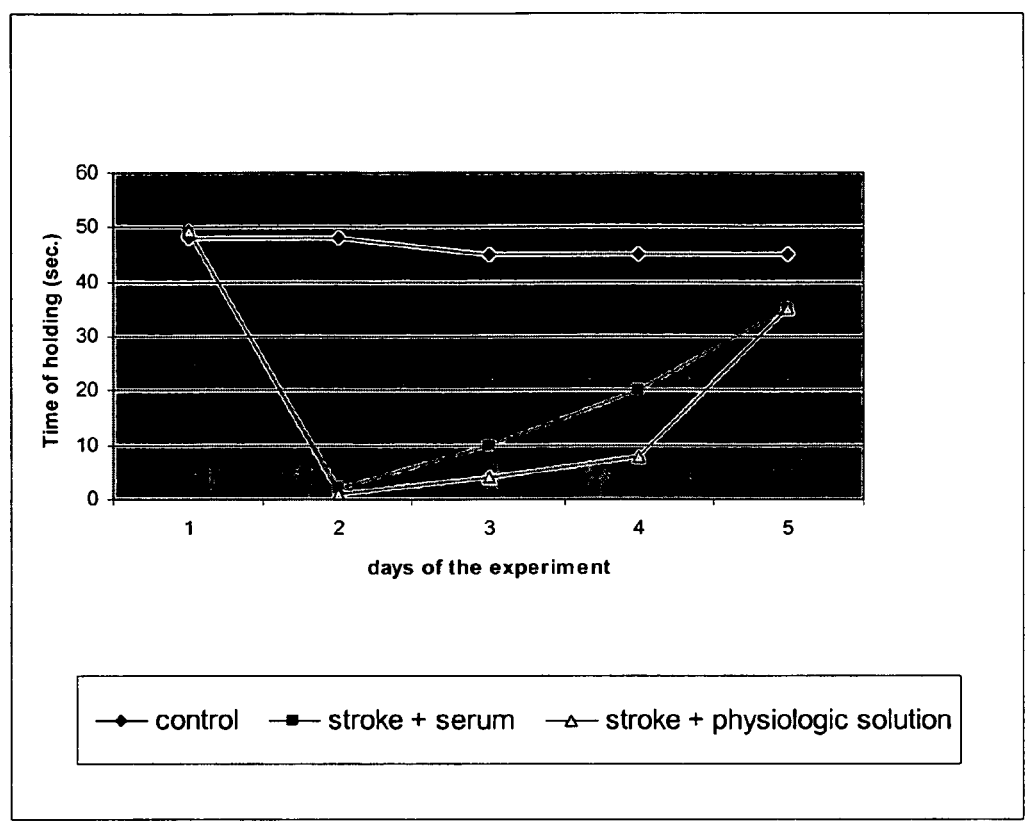

FIG. 12: Dynamic of the duration of the holding of rats on a horizontal bar. The graph depicts the time of holding (in sec.) of control rats or rats with an induced stroke treated with either serum or physiologic solution to a horizontal bar at different days of the experiment. The days of experiment have the meaning as in FIG. 3

Figure 13:
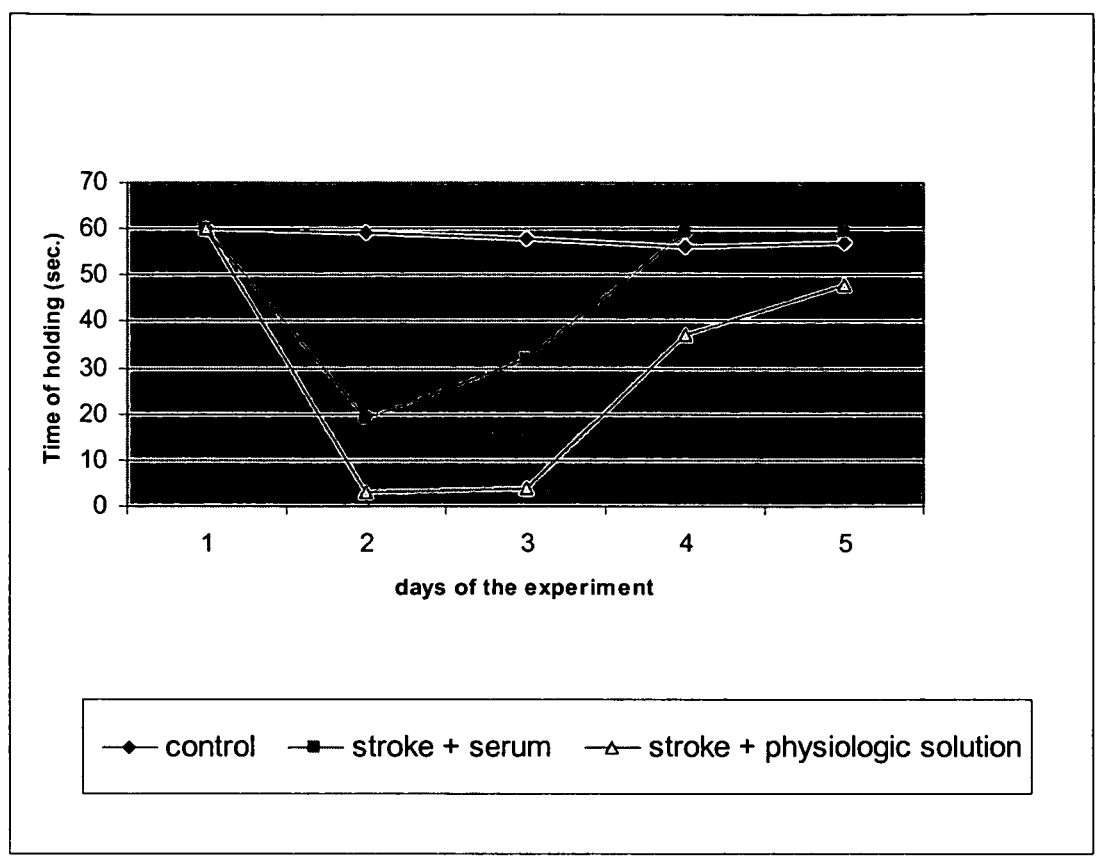

FIG. 13: Dynamic of the duration of the holding of the rats to a vertical grid. The graph depicts the time of holding (in sec.) of control rats or rats with an induced stroke treated with either serum or physiologic solution to a vertical grid at different days of the experiment. The days of experiment have the meaning as in FIG. 3

EXAMPLES

Example 1

Method of Obtaining Chicken Blood Treated by Electroshock

For the preparation of serum from chicken, the chicken were treated with an electroshock of grade II to III (electrical voltage 80-120 V, current 0.05 A, frequency 50 Hz, application time: 3 to 4 sec at the head) in a standard water bath. Blood was then drawn from the arteria carotis and further incubated at a temperature of 4 to 8° C. for 18 to 24 h in polyethylene flasks. After complete retraction of blood clots the flasks were spun at 3.000 rpm for between 20-30 minutes. The serum was separated from the blood clots and lyophilized under art known conditions. The flasks with the lyophilized serum were treated on a RZ-100-M apparatus with 20-30 kGy, preferably at around 25 kGy using $^{60}Co$ as a gamma radiation source for 3 to 4 h. Typically the dried serum is placed into a paper bag of a size of 70×75×200 mm during irradiation. Radiation strength is adapted to provide about 4.5 kGy/h in the middle of the bag. The treated serum was stored at a temperature of between 4 to 8° C. for later use.

Example 2

Determination of the Effect of biological Active Blood Serum on Experimentally Induced Ischemic Stroke in Male Wistar Rats The effects of the biological active blood serum of the present invention on an experimentally induced ischemic stroke in male rats was investigated. To investigate the effect an established animal model of ischemic stroke was used which involved the restriction of the arteria carotis at the base of the skull of a rat. The experiments involved 70 male wistar rats (body weight in the range of 210-240 g) out of which 60 animals were subjected to the artificial induction of an ischemic stroke and 10 were assigned to the control group, which were only treated with a physiologic solution (1 ml intraperitoneal). The animals were obtained from a Russian breeding plant (Stolbowaja of the Russian Academy of Medical Sciences).

Prior to the experiments 10 rats were placed into standard cages for at least 7 days to accustom them to at libido conditions, i.e. unlimited supply of food and water. During that period the animals were also subjected to the various behavioural tests which were also later used to assess the effectiveness of the biological active serum on stroke. The administered tests involved the below outlined behavioural tests, i.e. "open field" test, the "righting reflex", the ability to hold on to a horizontal beam or to a vertical grid as well as the pain sensitivity in the "hot plate" test. Animals which did not behave according to the standards established for normal untreated animals or which exhibited significant deviations were excluded from subsequent tests. The 60 animals in which a stroke was experimentally induced were anaesthetised with chloral hydrate (400 mg/kg intraperitoneal) and the arteria carotis was constricted at its entry into the base of the skull with a suture wherein the inner suture was carried out with "cat gut" sutures and the outer with surgical silk. Half of the animals undergoing the surgical procedure (30 animals) which were assigned to the group treated with biological active serum, were treated 30 minutes prior to surgical intervention with 100 mg/kg biological active serum comprised in 1 ml, which was injected intraperitoneally, and the same amount was administered daily for the following 21 days. The other half of the animals surgically treated to induce stroke-like symptoms was treated according to the same administration scheme, however, with 1 ml of a physiological solution at each administration. Experiments were carried out at about the same time of the day (between 12:00 to 15:00 o'clock each day). 24 hours after the surgical procedure the animals were tested in a panel of behavioural tests outlined below and 30 minutes prior to the test the animals were injected either with biological active serum or physiological solution depending on the group to the which they were assigned. 28 hours after the operation some animals were sacrificed the brain was removed and stored in ethanol solution for further histological examination. The brains of all animals which died during the experiments were stored similarly.

Behavioural Tests

The behavioural tests were carried out in 5 consecutive tests of 3 minute duration each day.

The days of the experiments were as follows:

Day 1: preoperative application of the test

Day 2: 24 hours postoperative

Day 3: 7 days postoperative

Day 4: 14 days postoperative

Day 5: 21 days postoperative

"Open Field" Test

One rat was placed on a brightly illuminated field (1 m×1 m) with lines drawn on the surface of the field. The movement and behaviour of the rat was observed for 3 minutes. The following parameters were evaluated during that time:

1. latency phase for leaving the middle of the open field,
2. horizontal movement activity (the number of squares frequented by the rat was determined),
3. vertical "curiosity activity" (it was determined how often the rat was uprighting itself),
4. number of movements towards the middle of the field,
5. number of movements within the middle of the field,
6. "grooming" activity of the rat,
7. number of bolus releases of the rat,
8. number of times the rat urinated.

From the relation of the performance figure of the movement activity (performance figures: 2 and 3), the "curiosity activity" (performance figures 2-5) and the emotionality (performance figures 1, 6-8) and the control and test groups as well as based on the change of the performance figures during the course of the tests it is possible to determine the effect of the biological active substance on psychical, emotional and neurological consequences of stroke. Furthermore, the tests allowed a first evaluation of the influence of the biological active blood serum on the locomotive function and coordination of movement.

"Hot Plate" Test

The "hot plate" test served the purpose of determining the pain reaction under thermic influence. The rat was carefully placed in a clean cylinder of 25 cm height with a heatable bottom plate with a diameter of 30 cm at a start temperature of 52° C. Two further temperatures (55° C. and 58° C.) were consecutively applied with 10 seconds separation until typical reactions occurred. If the animals did not show any reaction at 58° C. within 10 seconds the highest rate of analgesia was noted. The analgesia was scored according to a four-point system. The following reactions which reflect an analgesia (nociception) were noted:

1. removing and licking of the front paw "grooming" (nociceptive reaction),
2. removing and licking of the hind paws,
3. sound reactions and attempts to avoid the chamber.

"Righting Reflex" Test

The animals were put on their back and the time required to return to their normal position was measured. Animals not affected immediately returned to their normal position. After the induced stroke this "righting" can be slowed down or be entirely absent. The ability to return into a normal position is observed for 30 seconds.

Paw Pinch Reflex

The bending of the extremities as a reaction to the excitation of the hind paw with a preparative needle was investigated. The reflex is coordinated on the level of the spine of the nervous system.

Muscle Coordination Test

These tests assess the ability of a rat to hold on to a horizontal beam and to hold on to a vertical grid. For the first test the ability of the rat to hold to a horizontal beam with a diameter of 1.5 cm which was placed at a height of 50 cm above a laboratory bench was registered. For the second test the length of time was measured that the rat was capable of holding on to a vertical grid with a grid size of 50 cm$^2$ and a mesh size of 1.5 cm$^2$. The distance to the laboratory bench was 90 cm.

Both tests demonstrate the ability to coordinate the body position within the room and demonstrate the physical endurance of the rat.

Statistical Evaluation

The standard deviation was determined by non parameteric statistic (Fisher method) (E. B. Googler, A. A. Genken; application of non-parametric criteria in medical biological research (1973)).

Results

Of the 60 rats with a restricted arteria carotis, 27 animals died within 21 days, 8 of the deceased animals belonged to the group treated with the biological active serum and 19 of the animals belong to the group treated with a physiologic solution only (p<0.05) (see FIG. 1). The time course of the occurrence of the deaths of the animals is depicted in FIG. 2.

Results in the "Open Field" Tests

The following difference between the surgical treated and untreated animals was noted:

The latency phase for the begin of the activity increased within the 21$^{st}$ hours after the surgical treatment in the group "stroke+serum" only marginally while in the group "stroke+ physiologic solution" increased significantly (p<0.05).

The numerical results for the surgical treated groups 24 hours, 7 days, 14 days or 21 days postoperative for each of the test parameters is depicted in table 1 for rats in the group "stroke+serum" and in table 2 for rats of the group "stroke+ physiological solution".

TABLE 1

Behaviour of rats of group "stroke + serum" in the "open field" test

| | Weight (g) | Latency phase (sec.) | Frequenting of squares | Movement to the middle of the field | Movement within the middle of the field | Number of upright positions | "Grooming" | Bolus | Urination |
|---|---|---|---|---|---|---|---|---|---|
| preoperative | 217.7 ± 4.3 | 1.1 ± 1.1 | 88.3 ± 26.2 | 0.1 ± 0.3 | 0.4 ± 0.5 | 9.9 ± 3.1 | 3.6 ± 1.9 | 3.6 ± 1.8 | 0.3 ± 0.5 |
| 24 h postoperative | 214.4 ± 4.2 | 1.3 ± 0.8 | 55.4 ± 19.5 | 0.1 ± 0.3 | 0.4 ± 0.6 | 0 | 2.0 ± 0.9 | 2.8 ± 1.5 | 0.2 ± 0.4 |
| 7 d postoperative | 219.4 ± 4.2 | 0.7 ± 0.6 | 38.9 ± 14.6 | 0.1 ± 0.3 | 0.3 ± 0.5 | 2.2 ± 1.2 | 2.7 ± 1.1 | 2.4 ± 1.5 | 0.1 ± 0.4 |
| 14 d postoperative | 224.6 ± 3.9 | 0.7 ± 0.5 | 28.9 ± 9.4 | 0 | 0.3 ± 0.5 | 3.2 ± 1.6 | 3.3 ± 1.3 | 1.9 ± 1.2 | 0.2 ± 0.4 |
| 21 d postoperative | 226.4 ± 4.2 | 0.7 ± 0.5 | 24.6 ± 9.0 | 0 | 0.2 ± 0.4 | 2.9 ± 1.5 | 2.9 ± 1.2 | 1.3 ± 0.8 | 0.1 ± 0.3 |

TABLE 2

Behaviour of the rats of group "stroke + physiologic solution" in the "open field" test

| | Weight (g) | Latency phase (sec.) | Frequenting of squares | Movement to the middle of the field | Movement within the middle of the field | Number of upright positions | "GrooMing" | Bolus | Urination |
|---|---|---|---|---|---|---|---|---|---|
| preoperative | 221.3 ± 5.8 | 0.7 ± 0.8 | 73.8 ± 34.0 | 0.3 ± 0.4 | 0.6 ± 0.7 | 8.4 ± 4.1 | 4.7 ± 1.6 | 2.9 ± 1.6 | 0.2 ± 0.4 |
| 24 h postoperative | 218.8 ± 4.9 | 3.9* ± 1.7 | 17.4* ± 8.3 | 0 | 0.2 ± 0.4 | 0 | 1.0 ± 0.9 | 1.2 ± 0.7 | 0.1 ± 0.3 |
| 7 d postoperative | 219.1 ± 5.3 | 2.5 ± 0.8 | 38.2 ± 12.6 | 0 | 0.1 ± 0.3 | 0.3 ± 0.5 | 0.4 ± 0.6 | 0.6 ± 0.7 | 0.1 ± 0.3 |
| 14 d postoperative | 220.0 ± 5.1 | 1.8 ± 0.6 | 37.2 ± 9.1 | 0 | 0 | 1.4 ± 1.1 | 1.5 ± 1.3 | 0.5 ± 0.5 | 0.1 ± 0.3 |
| 21 d postoperative | 222.8 ± 4.8 | 0.8 ± 0.4 | 22.1 ± 7.4 | 0 | 0.1 ± 0.3 | 1.7 ± 0.7 | 2.9 ± 1.1 | 1.4 ± 0.9 | 0.1 ± 0.4 |

*p < 0.05

The graphical depiction of the differences of the dynamic of the latency phase for leaving the middle of the field in the "open field" test is shown in FIG. 3. It is evident that in the group "stroke+serum" the values of the latency approaches the results for the control group, while the "stroke+physiologic solution" group lacks behind those two other groups during the course of the experiment. Such a quick recovery of the latency resembling the latency of the control group indicates a re-establishment of the decision making function within the group.

It is also observed that the number of frequented squares slowly increases during the course of the experiments in the control group and the "stroke+serum" group while this number significantly decreases in the group "stroke+physiologic solution" ($p \leq 0.05$), which indicates a stronger "attenuation effect" in the group "stroke+physiologic solution" than in the group "stroke+serum" (see FIG. 4).

The movement towards the middle of the open field does not show a significant difference in any of the three groups investigated. However, the number of vertical activity is only slowly reduced in the control group while it is reduced to zero in both surgically treated groups. This effect is potentially due to pain in the neck and shoulder area due to the surgical procedure (see FIG. 5). Stereotype activity (as determined by the number of "grooming" acts) more rapidly approaches the numbers observed in the control group only for the group "stroke+serum" while this behaviour is exhibited less pronounced in the group "stroke+physiologic solution" (see FIG. 6).

The dynamic of the release of bolus and the frequency of the urination was almost identical for all three groups (see FIGS. 7 and 8).

The sensitivity to pain was determined with a "hot plate" test and it is notable that 24 hours postoperative the pain sensitivity was reduced for both surgically treated groups with statistic significance ($p<0.05$). However, the pain sensitivity reached almost control group levels 7 days after the surgical procedure in the group "stroke+serum" while the pain sensitivity in the group "stroke+physiologic solution" was still lower 21 days after the surgical procedure. The actual values are depicted in Table 3 below.

between the control group and the group "stroke+physiologic solution" was larger than the difference between the control group and the group "stroke+serum" (see FIG. 11).

Similar results were obtained for the muscle coordination tests which also showed that the group "stroke+serum" did more closely resemble the control group than did the group "stroke+physiologic solution" (see FIG. 12 and FIG. 13). The significant differences between the holding test on a horizontal beam and the holding test at a vertical grid might be due to injuries to the muscles of the neck and shoulder of the rats inflicted during the surgical procedures which hampered the holding of the rat to the horizontal bar. This interpretation is corroborated by the fact that the rats were much better in holding on to the vertical grid in the vertical grid test presumably because they were able to use their non-injured neck muscles and muscles of the hind paws in this test.

Taken together it appears that after an experimental induction of an injury resembling an ischemic stroke the values for locomotive activity and curiosity in the "open field" test is significantly better in animals treated with the biological active serum and in many instances approaches the control group. In the "hot plate" test the sensitivity of animals treated with the biological active serum to pain increases, the latency phase for the righting reflex decreases and the paw pain reflex increases, if compared to animals treated with physiologic solution. In addition, the duration of holding on to a horizontal bar or to a vertical grid also significantly increases upon treatment with biological active serum. It is also evident that the daily application of the biological active serum decreases the number of animals dying in response to the surgical procedure. Taken together is has been established that the symptoms associated with the experimental stroke model in rats are ameliorated by the administration of the biological active blood serum of the present invention and in many instances return to control levels.

TABLE 3

Dynamic of the pain sensitivity of the rats of the various groups

|  | 0 | 24 h | 7 days | 14 days | 21 days |
|---|---|---|---|---|---|
| Physiologic solution | 2.0 ± 0.0 | 2.0 ± 0.0 | 2.0 ± 0.0 | 2.0 ± 0.0 | 2.0 ± 0.0 |
| Stroke + physiologic solution | 2.0 ± 0.2 | 2.8 ± 0.4 | 2.7 ± 0.4 | 2.5 ± 0.5 | 2.3 ± 0.5 |
| stroke + serum | 2.0 ± 0.0 | 2.7 ± 0.4 | 2.1 ± 0.3 | 2.1 ± 0.3 | 2.0 ± 0.0 |

The numbers depicted in Table 3 are graphically shown in FIG. 9.

The "righting reflex" is significantly different for the group "stroke+physiologic solution", if compared to the control group and the group "stroke+serum". The latency phase in this group is significantly higher and only slowly returns to the normal levels but does not reach normal levels within the duration of the experiment (see FIG. 10). The paw pain reflex was present in every control animal, however, was not inducible in all surgically treated rats. However, the difference Example 3

Determination of the Cerebroprotective Effect of Biological Active Blood Serum in a Model of Cerebral Haemorrhage in Rats, with Evaluation of Neurological Deficits, the Impairment of Cognitive Functions, Level of Anxiety and Survival Rate Example 3.1

Method of Post-Traumatic Intracerebral Haematoma (Cerebral Haemorrhage)

At present the cerebroprotective effect of a substance is experimentally studied using various models of cerebrovas cular insult and cerebral haemorrhage (T. A. Voronina. Hypoxia and memory. Pecularities of the effects and the application of nootropic substances/*Information sheet of the Russian Academy of Medical Sciences*, Vol. 9, pp. 27-33 (2000); A. N. Makarenko, N. S. Kositsyn, S. V. Karpenko, V. A. Mishina. Inventor Document No. 1767518 of Mar. 11, 1990; A. Jackowski, A. Crockard, G. Burnstock, R. Ross Russell, F. Kristek. The time course of intracranial pathophysiological changes following experimental subarachnoid haemorrhage in the rat/*Journal of Cerebral Blood Flow and Metabolism*, v. 10, pp. 835-849 (1990); S. Smith, H. Hodges, P. Sowinski. Long-term beneficial effects of BW619C89 on neurological deficit, cognitive deficit and brain damage after middle cerebral artery occlusion in the rat/*Neuroscience*, v. 77, #4, pp. 1123-1135 (1997)), which are mostly caused by compression or destruction of the meningeal vessels or deep brain structure in various animals (e.g. rabbits, rats).

The present study used the method of A. N. Makarenko et al. (1990) to model a local cerebral haemorrhage (post-traumatic intracerebral haematoma). The experiments were carried out on white non pure-bred male rats with a weight of 200 to 250 g. The rats were kept in a vivarium with free access to food and water.

Cranial trepanation was performed on rats anaesthetized with chloral hydrate (400 mg/kg, intramuscular) in order to cause a stroke and then the brain tissue in the region of the internal capsule was destroyed using special equipment (mandrin (needle drain) scalpel) and stereotaxis, followed (after 2-3 minutes) by a blood infusion at the site of the lesion (sublingual blood removal (0.02-0.03 ml). This method enables a local bilateral haemorrhagic insult in the region of the internal capsule (diameter 2 mm, depth 3 mm) to be achieved without significant damage to the brain or neocortical structures located above. 42% of the rats died from stroke during or immediately after the procedure. Various neurological, cognitive and other behavioural disorders were then determined in the surviving animals with cerebral haemorrhage.

The neurological deficit, movement coordination, muscle tone, orientation-exploratory behaviour and mortality of the rats with cerebral haemorrhage (CH) were determined 24 hours after the operation.

The evolution of impairments caused by the post-traumatic intracerebral haematoma and the effect of biological active blood serum on the behaviour of the rats were observed in the 14 days after the intervention, and the behaviour and condition of the animals determined on the first, third, seventh and fourteenth day after the intervention.

The animals were divided into four groups:
intact rats (Group I);
pseudo-operated rats which had undergone trepanation under sedation (Group II);
Animals with cerebral haemorrhage (Group III),
Animals with cerebral haemorrhage which received biological active blood serum (Group IV).

The biological active blood serum preparation was administered in a dosage of 500 mg/kg (intragastric administration using a special probe) 5 hours after the intervention. It was then administered once daily over seven days.

The physiological solution was administered intragastrically in equivalent amounts for the test animals—Groups I, II and III.

A range of conventional methods was used for evaluating behavioural disorders and the condition of the animals after cerebral haemorrhage.

1. For Assessment of Neurological Status

Method for assessing neurological deficits using the McGraw stroke index, modified by I. V. Gannushkina (I. V. Gannushkina. Functional angioarchitecture of the brain/Medicine, Moscow, p. 224 (1997), I. V. Gannushkina. Pathophysiological mechanisms of impairments to brain circulation and new trends in their prophylaxis and treatment/*Neuropathologist and Psychiatrist Journal*, No. 1, pp. 14-18 (1996));

Method for determining muscle tone;

Method for determining movement coordination.

2. For assessment of cognitive functions—passive avoidance conditioned reflex (PACR) in light/dark apparatus (Equipment: Lafayette Instrument Co., USA).

3. For assessment of orientation-exploratory behaviour—"open field" method.

4. Evaluating the effect of the preparation on the survival of the rats Mortality of the rats was registered over 14 days.

5. The statistical evaluation of data was carried out by calculating the arithmetic mean and confidence limits for P<0.05. To assess the accuracy of results, the data evaluation parameters were checked using the Student's t-Test and chi-squared ($\chi^2$) function of the "Biostat" computer program.

Example 3.2

Assessment of Neurological Status

Method for Assessing Neurological Deficits Using the McGraw Scale

Neurological deficits in the animals were determined using the McGraw stroke index in its modification by I. V. Gannushkina (1997, 1996). The severity of the condition was assessed according to the total number of points. The number of rats with slight symptoms of up to 2.5 points according to the stroke index (atonic movements, limb weakness, unilateral semiptosis, tremor, circular movements) and with severe manifestations of neurological impairment (from 3 to 10 points)—paresis and paralysis of limbs, together with position (see Table 1) were determined.

TABLE 4

Neurological function disorders according to the McGraw scale

| Neurological symptoms | Stroke index |
| --- | --- |
| Atonia, slow movement | 0.5 |
| Tremor | 1 |
| Unilateral semiptosis | 1 |
| Bilateral semiptosis | 1.5 |
| Limb weakness | 1.5 |
| Unilateral ptosis | 1.5 |
| Bilateral ptosis | 1.5 |
| Circular movements | 2 |
| Paresis of 1-4 limbs | 2.0-5.0 |
| Paralysis of 1-4 limbs | 3.0-6.0 |
| Comatose condition | 7 |
| Death | 10 |

Method for Determining Muscle Tone

For determining muscle tone a pull-up test on a horizontal bar was used (T. A. Voronina, S. B. Seredenin. Methodical guide to the study of the tranquilizing (anxiolytic) effect of pharmacological substances/*Guide to the experimental (preclinical) study of new pharmacological substances*, pp. 126-130 (2000)). The rats were placed with their front paws on a wire stretched at a height of 20-30 cm above the table. The intact rats with undamaged muscle tone quickly pulled themselves up and held onto the bar with four paws. If animals in the test group could not fulfil this requirement, it indicated impairment of muscle tone and a neurological deficit.

Method for Determining Movement Coordination.

For determining neurological deficits manifest as impaired movement coordination, the rats were placed on a horizontal bar of 4 cm diameter turning at a speed of 3 revolutions per minute (T. A. Voronina, S. B. Seredenin, 2000). If animals were unable to maintain their balance for 2 minutes it was considered an indication of impaired movement coordination.

Example 3.3

Assessment of Cognitive Functions

Method for Developing the Passive Avoidance Conditioned Reflex (PACR) Using a Light/Dark Apparatus (Lafayette Instrument Co, USA)

The examination was carried out in a standard unit for the passive avoidance acquired (conditioned) reflex from Lafayette Instrument Co. (USA). The unit consisted of a small platform positioned one metre from the floor and illuminated by a special lamp, and a dark compartment with an electrode floor which was connected to it. The rat was placed on the illuminated platform in front of the entrance to the dark compartment with its tail towards the entrance.

For the assessment of the hole reflex the latent time before it first entered the dark compartment was registered. The rat preferring the dark compartment moves over into it.

The rat then received a single pain stimulus in the dark compartment from an electric current (0.45 mA)—the training. The duration of this training (the stimulus) was determined by when animals left the dark area (T. A. Voronina, R. U. Ostrovskaya. Methodical guide to the study of the nootropic activity of pharmacological substances/*Guide to the experimental (preclinical) study of new pharmacological substances*, pp. 153-158 (2000)).

Testing of the passive avoidance conditioned reflex (maintenance of the neurogram) was carried out 24 hours after training and then three, seven and fourteen days after the surgical intervention. The animal was again placed on the illuminated platform and within 3 minutes, the latent time before first entering the dark compartment and the length of time the rat stayed in the dark compartment were recorded.

Example 3.4

Assessment of Orientation-Exploratory Behaviour

"Open Field" Test (T. A. Voronina, S. B. Seredenin, 2000)

The "open field" unit for rats comprised a compartment of dimensions 60×60 cm with a transparent cover. The compartment floor was uniformly divided by lines into 9 squares with 16 holes (openings) of 4 cm diameter. During the 3 minute stay of the rat in the open the following parameters were recorded: number of movements onto the hind paws (vertical movements), the number of passages from one square to another (horizontal movements) and the number of times the rat looked into a hole.

Example 3.5

Results

Assessment of Neurological Deficits Using McGraw Scale

When assessing neurological changes in test rats with cerebral haemorrhage it was found that on the first day after surgical intervention nearly all the animals (90-100%) showed neurological impairments in the form of atonia, slow movements and limb weakness; these impairments were found in 30-40% of the pseudo-operated rats. Severe neurological impairments, manifest as circular movements, paresis and limb paralysis, were not observed in the group of pseudo-operated rats, but were found in 40-30% of animals with cerebral haemorrhage.

When a single 500 mg/kg dose of the biological active blood serum preparation was administered, the incidence of neurological impairments was reduced. Slight impairments were found in 40-60% of the animals.

TABLE 5

Effect of biological active blood serum preparation (500 mg/kg, intra) on neurological deficit in rats after suffering cerebral haemorrhage (according to McGraw scale)

| Neurological symptoms | pseudo-operated | after a stroke | biological active blood serum |
|---|---|---|---|
| atonia, slow movements | 40 | 100 | 60 |
| limb weakness | 30 | 90 | 40* |
| circular movements | 0 | 40 | 0* |
| paresis 1-4 limbs | 0 | 30 | 20 |
| paralysis 1-4 limbs | 0 | 30 | 0* |

Number of animals with various neurological symptoms, % 1st day after intervention Animal group

*the accuracy of differences for rats with stroke for $P \leq 0.05$ ($\chi^2$)

Single administration of the biological active blood serum preparation thus reduces the extent of impaired neurological status in rats one day after a cerebral haemorrhage.

Determination of Muscle Tone in Pull Up Test on bar.

Determination of muscle tone in rats with cerebral haemorrhage showed that there was impaired muscle tone in a mean 40-50% of rats on the third day after the insult, and 33-36% of the animals on the seventh-fourteenth day. In animals receiving biological active blood serum, impaired muscle tone observed on the first and third day was 33%, on the seventh day 25%, while the figures had fallen to 16% on the fourteenth day and were statistically accurate when compared to the data of insult animals (see Table 6).

TABLE 6

Effect of biological active blood serum on muscle tone of animals after cerebral haemorrhage in horizontal bar test

| | Animals that did not pull up on the horizontal bar, in numbers and % | | | | | | | |
|---|---|---|---|---|---|---|---|---|
| | 1st day | | 3rd day | | 7th day | | 14th day | |
| Animal group | no. | % | no. | % | no. | % | no. | % |
| Intact (no surgical intervention) | 0/10 | 0 | 0/10 | 0 | 0/10 | 0 | 0/10 | 0 |
| Pseudo-operated | 1/10 | 10 | 1/10 | 10 | 2/10 | 20 | 0/9 | 0 |
| Insult | 10/24 | 41* | 9/19 | 47* | 4/12 | 33 | 4/11 | 36 |
| Insult + biological active blood serum | 4/12 | 33 | 4/12 | 33 | 3/12 | 25 | 2/12 | 16** |

*the accuracy of differences for pseudo-operated rats for $P \leq 0.05$ ($\chi^2$)
**the accuracy of differences for rats with stroke for $P \leq 0.05$ ($\chi^2$)

Determination of Movement Coordination in Revolving Bar Test

Testing of coordination impairments in rats with cerebral haemorrhage showed that 46-47% of surviving animals had impaired movement coordination on the first-third day, and 42-45% of surviving animals on the seventh-fourteenth day.

A 500 mg/kg dose of the biological active blood serum preparation reduced the impairments to movement coordination. This was particularly marked and statistically reliable on the seventh-fourteenth day after the stroke.

TABLE 7

Effect of biological active blood serum preparation on movement coordination of animals after cerebral haemorrhage in revolving bar test

| | Animals that did not remain on the revolving bar (3 rpm) for 2 minutes, in numbers and % | | | | | | | |
|---|---|---|---|---|---|---|---|---|
| | 1st day | | 3rd day | | 7th day | | 14th day | |
| Animal group | no. | % | no. | % | no. | % | no. | % |
| Intact (no surgical intervention) | 0/10 | 0 | 0/10 | 0 | 0/10 | 0 | 0/10 | 0 |
| Pseudo-operated | 2/10 | 20 | 3/10 | 30 | 2/10 | 20 | 1/9 | 10 |
| Insult | 11/24 | 46* | 9/19 | 47 | 5/12 | 42* | 5/11 | 45* |
| Insult + biological active blood serum | 5/12 | 42 | 4/12 | 33 | 0/12 | 0** | 0/12 | 0** |

*the accuracy of differences von den pseudo-operated rats for $P \leq 0.05$ ($\chi^2$)
**the accuracy of differences for rats with cerebral haemorrhage for $P \leq 0.05$ ($\chi^2$)

Effect of Biological Active Blood Serum Preparation on Training and Memory Retention and on Execution of Hole Reflex of Animals with Cerebral Haemorrhage The passive avoidance conditioned reflex (PACR) is based on the innate hole reflex of rodents—their instinct to seek out a confined dark space. When they have spent time in an illuminated compartment, the test rats rapidly move over to the dark compartment after a short latent period. The study on the effect of the biological active blood serum preparation showed that after training there were no adverse effects on the hole reflex for any of the animals (intact, pseudo-operated, rats with cerebral haemorrhage or rats that had been administered biological active blood serum). But although the hole reflex for rats with cerebral haemorrhage was not impaired, the latent time for the reflex to be executed was increased. The biological active blood serum preparation did not impair execution of the hole reflex.

TABLE 8

Effect of biological active blood serum on the execution of the hole reflex

| Animal group | Latent time before entering the dark compartment after training (hole reflex) 1st day after intervention |
|---|---|
| Intact animals (no surgical intervention) | 9.8 ± 1.2 |
| Pseudo-operated | 10.03 ± 0.9 |
| After insult | 30.2 ± 10.1 |
| biological active blood serum | 34.6 ± 5.8 |

Effect of the Biological Active Blood Serum Preparation on the Memory Retention of Animals It was found that for the test group that had received the physiological solution during the study (intact group), when the passive avoidance conditioned reflex (PACR) was reproduced even 24 hours after training (pain stimulus in the dark compartment), 80% of the animals remembered the electric shock and did not enter the "dangerous" dark compartment over the entire period of observation.

In the group of pseudo-operated animals one day after training, 70% remembered the electric shock in the dark compartment and would no longer enter it.

In the group with the cerebral haemorrhage, 25% of animals no longer entered the dark compartment, i.e. they remembered the electric shock, and in 75% of rats memory was impaired. When the passive avoidance conditioned reflex (PACR) was reproduced on the 14th day after surgical intervention, only 9% of the rats still retained a memory, the figures for intact and pseudo-operated rats after this time were 60% and 58% respectively. In addition, rats with a stroke had consistently reduced latent time for entering the dark compartment, which also indicates the impaired memory of these animals.

The biological active blood serum preparation did not reliably affect reproduction of the passive avoidance conditioned reflex (PACR) one day after training. But a statistically reliable increase in the latent time of the reflex was observed in the group of rats that had been administered biological active blood serum when the reflex was reproduced after 14 days.

TABLE 9

Effect of biological active blood serum on reproduction of passive avoidance conditioned reflex (PACR) in rats with post-traumatic intracerebral haematoma

| | Reproduction of the passive avoidance conditioned reflex (PACR) after: | | | |
|---|---|---|---|---|
| | 24 hours after training | | 3 days | |
| Animal group | Latent time before entering the dark compartment | Number of rats that did not enter the dark compartment, % | Latent time before entering the dark compartment, % | Number of rats that did not enter the dark compartment, % |
| Intact (no surgical intervention) | 155.0 ± 25.0 | 80 | 153.5 ± 15.3 | 80 |
| Pseudo-operated | 140.1 ± 16.3 | 70 | 138.6 ± 19.4 | 65 |
| Insult | 66.3 ± 38.4* | 25* | 71.3 ± 41.1* | 28 |
| Insult + biological active blood serum | 103.3 ± 23.2 | 50 | 131.2 ± 19.7 | 58 |

The biological active blood serum preparation administered as a single dose of 500 mg/kg 5 hours after surgical intervention increased by up to 50% the number of animals with retained memory (animals with the cerebral haemorrhage—25%) and increased (by 1.6 times) the latent time before entering the dangerous dark compartment. But this positive effect was not statistically reliable. Three days after the CH (cerebral haemorrhage) intervention and after 3 doses of biological active blood serum a positive effect of the preparation on memory was also recorded. However, this positive effect was also statistically unreliable.

Continuation of Table 9

| | Reproduction of passive avoidance conditioned reflex (PACR) after: | | | |
|---|---|---|---|---|
| | 7 days | | 14 days | |
| Animal group | Latent time before entering the dark compartment | Number of rats that did not enter the dark compartment, % | Latent time before entering the dark compartment, % | Number of rats that did not enter the dark compartment, % |
| Intact | 142.0 ± 18.4 | 75 | 130.4 ± 27.1 | 60 |
| Pseudo-operated | 123.7 ± 21.0 | 60 | 112.4 ± 21.6 | 58 |
| Insult | 25.0 ± 2.9* | 16* | 21.7 ± 10.2* | 9* |
| Insult + biological active blood serum | 121.7 ± 22.1** | 50** | 113.3 ± 23.9** | 58** |

*the accuracy of differences of pseudo-operated rats for $P \leq 0.05$ (Student's t test; $\chi^2$)
**the accuracy of differences for rats with stroke for $P \leq 0.05$ (Student's t test; $\chi^2$)

After the 7th and 14th day the intact and pseudo-operated rats remembered the negative situation well and executed the passive avoidance conditioned reflex (PACR). However memory of the pain stimulus in the dark compartment was reliably impaired in rats with cerebral haemorrhage on the 7th-14th day following the intervention.

There was more marked impairment of memory compared to the values after the 1st and 3rd day following intervention. For example, after the 7th day only 16% of animals remembered the negative stimulus and the remaining rats had already entered the dangerous dark compartment after 25 seconds. And after 14 days the passive avoidance conditioned reflex (PACR) was only retained by 9% of the animals (Table 9).

The biological active blood serum preparation, which was administered to the rats in a dose of 500 mg/kg within 7 days, reestablished memory in the post-cerebral period (the time after the stroke) on the 7th and 14th day after the CH intervention. The biological active blood serum preparation was observed to produce a statistically reliable increase in the number of animals able to remember the negative situation (after the 7th day—50%, and after the 14th day—58%). The latent time before entering the dangerous dark compartment also increased by ca. 5 times compared to the insult rats (Table 9).

When repeatedly administered, the biological active blood serum preparation thus has the ability to restore memory which has been impaired due to cerebral haemorrhage, using a passive avoidance conditioned reflex (PACR) as a model.

Effect of the Biological Active Blood Serum Preparation on the Orientation-Exploratory Behaviour of Rats with Cerebral Haemorrhage Investigation of orientation-exploratory behaviour using an "open field" method showed that on the first day after intervention there was a significant, almost 2 fold reduction in summed values of movement activity and exploratory behaviour in rats with cerebral haemorrhage. The same parameters of rat behaviour were also recorded on the 14th day after cerebral haemorrhage, although the animals were to some extent more active.

When examining the effect of the biological active blood serum preparation one day after the cerebral haemorrhage, the summed values of behaviour had been increased to the level of those in the group of pseudo-operated animals.

TABLE 10

Effect of the biological active blood serum preparation on orientation-exploratory behaviour and the movement activity of animals after cerebral haemorrhage using an "open field" method

| Animal group | Horizontal movement | Vertical movement | Investigation of openings | Summed values |
|---|---|---|---|---|
| 1st day after intervention | | | | |
| Intact | 12.6 ± 2.2 | 6.6 ± 1.3 | 3.0 ± 0.8 | 22.2 ± 5.4 |
| Pseudo-operated | 13.7 ± 1.8 | 3.0 ± 0.5 | 3.1 ± 0.5 | 19.8 ± 2.2 |
| Insult | 6.3 ± 1.2* | 2.5 ± 0.6 | 1.9 ± 0.4 | 10.7 ± 1.9* |
| Insult + biological active blood serum | 14.4 ± 3.0** | 5.1 ± 2.9 | 1.2 ± 0.2 | 20.0 ± 4.0** |
| 3rd day after intervention | | | | |
| Intact | 11.0 ± 1.1 | 5.8 ± 0.9 | 3.5 ± 0.7 | 20.3 ± 2.3 |
| Pseudo-operated | 12.5 ± 1.1 | 2.9 ± 0.6 | 3.0 ± 0.4 | 18.4 ± 2.0 |
| Insult | 5.9 ± 1.3* | 2.5 ± 0.5 | 1.6 ± 0.3 | 10.0 ± 1.4* |
| Insult + biological active blood serum | 11.7 ± 2.5** | 4.6 ± 3.3 | 2.2 ± 0.4 | 18.5 ± 3.3** |
| 7th day after intervention | | | | |
| Intact | 12.1 ± 2.1 | 5.3 ± 1.3 | 4.4 ± 1.1 | 21.8 ± 4.9 |
| Pseudo-operated | 13.9 ± 2.0 | 4.3 ± 3.1 | 2.3 ± 0.4 | 20.5 ± 3.3 |
| Insult | 7.4 ± 1.8 | 3.9 ± 1.1 | 2.1 ± 0.4 | 13.4 ± 2.9 |
| Insult + biological active blood serum | 13.9 ± 2.6 | 4.8 ± 2.5 | 2.7 ± 0.3 | 21.4 ± 3.1 |
| 14th day after intervention | | | | |
| Intact | 11.7 ± 2.3 | 5.1 ± 1.1 | 3.8 ± 1.0 | 20.6 ± 5.9 |
| Pseudo-operated | 14.5 ± 2.3 | 7.1 ± 1.3 | 4.3 ± 0.7 | 25.9 ± 3.7 |
| Insult | 8.2 ± 2.2* | 4.2 ± 1.2 | 3.6 ± 1.1 | 16.0 ± 3.9* |
| Insult + biological active blood serum | 13.0 ± 2.8** | 6.7 ± 1.2 | 3.7 ± 0.6 | 23.4 ± 3.6** |

*the accuracy of differences of pseudo-operated rats for $P \leq 0.05$ (Student's t test)
**the accuracy of differences of rats with stroke for $P \leq 0.05$ (Student's t test)

Evaluation of Effect of Biological Active Blood Serum Preparation on Survival of Rats 42% of the rats died during the surgical intervention or immediately after.

The animals surviving in the first hours after the cerebral haemorrhage were observed over 14 days. As can be seen in Table 11, no fatalities were observed in the group of pseudo-operated rats from the first to the seventh day after intervention, and 1 out of 10 rats died on the 14th day.

In the group of rats with the cerebral haemorrhage, 20% of the animals died in the first day, and the number rose to 63% by the 14th day. The biological active blood serum preparation, which was administered in a dosage of 500 mg/kg intra daily for 7 days, completely prevented mortality in rats with the cerebral haemorrhage.

TABLE 11

Effect of biological active blood serum preparation on survival of animals after cerebral haemorrhage

| | Number of animals dying in 14 days after cerebral haemorrhage | | | | | | | |
|---|---|---|---|---|---|---|---|---|
| | 1st day | | 3rd day | | 7th day | | 14th day | |
| Animal group | no. | % | no. | % | no. | % | no. | % |
| Pseudo-operated | 0/10 | 0 | 0/10 | 0 | 0/10 | 0 | 1/10 | 10 |
| Insult | 6/30 | 20* | 5/24 | 21* | 7/19 | 37* | 1/12 | 8* |
| Insult + biological active blood serum | 0/12 | 0** | 1/12 | 8* | 1/12 | 8** | 0/12 | 0** |

*the accuracy of differences of pseudo-operated rats for $P \leq 0.05$ ($\chi^2$)
**the accuracy of differences of rats with stroke for $P \leq 0.05$ ($\chi^2$)

Example 3.6

Summary of the Results of Examples 3.1 to 3.5

The above described investigations showed that the rats with cerebral haemorrhage (post-traumatic intracerebral haematoma) had a pronounced neurological deficit, impairment of movement coordination, impairment of training processes and memory, and higher numbers of animal fatalities compared with the pseudo-operated animals. The intensification of pathological symptoms was recorded up to the 14th day of observations.

After being administered to the animals in a dosage of 500 mg/kg 5 hours after intervention, and then for 7 days, the biological active blood serum preparation resulted in significant improvements to post-cerebral impairments. The preparation improved parameters indicating neurological status according to the McGraw scale already one day after the stroke, and when used similarly to a course of treatment, it increased muscle tone and improved movement coordination by the 7th and 14th day following the stroke. When administered repeatedly the preparation improved impaired memory and improved reproduction of the passive avoidance conditioned reflex on the 7th and 14th day after the insult. A particularly marked effect of the biological active blood serum preparation was its ability to almost completely prevent mortality in animals with the cerebral haemorrhage.

The biological active blood serum preparation (500 mg/kg, intra) thus shows pronounced cerebroprotective activity in rats when administered over 7 days, using a model of cerebral haemorrhage (post-traumatic intracerebral haematoma). This effect is manifest as an improvement of neurological status, general behaviour, cognitive functions and a reduction in animal mortality rates.

Example 4

Determination of the Cerebroprotective Effect of Biological Active Blood Serum in the Form of Suppositories in a Model of Cerebral Haemorrhage in Rats, with Evaluation of Neurological Deficits, the Impairment of Cognitive Functions, Level of Anxiety and Survival Rate Example 4.1

Method of Post-Traumatic Intracerebral Haematoma (Cerebral Haemorrhage)

Cranial trepanation was performed as described in Example 3.1. 45% of the rats died from stroke during or immediately after the procedure.

As described in Example 3.1, the evolution of impairments caused by the post-traumatic intracerebral haematoma and the effect of biological active blood serum in the form of suppositories on the behaviour of the rats were observed in the 14 days after the intervention, and the behaviour and condition of the animals determined on the first, third, seventh and fourteenth day after the intervention.

The animals were divided into four groups:
intact rats (Group I);
pseudo-operated rats which had undergone trepanation under sedation without destruction of brain tissue (Group II);
Animals with cerebral haemorrhage (Group III),
Animals with cerebral haemorrhage which received biological active blood serum suppositories (Group IV).

The biological active blood serum preparation in the form of suppositories was administered rectally in a dosage of 100 mg/kg 5 hours after the intervention. It was then administered once daily over seven days.

The physiological solution was administered rectally in equivalent amounts for the test animals of Groups I, II and III.

Example 4.2

Assessment of Neurological Status

The neurological status of the animals was assessed as described in Example 3.2.

Example 4.3

Assessment of Cognitive Functions

The cognitive functions of the animals were assessed as described in Example 3.3

Example 4.4

Assessment of Orientation-Exploratory Behaviour

"Open Field" Test (T. A. Voronina, S. B. Seredenin, 2000)

The "open field" unit for rats comprised a compartment of dimensions 120×120 cm with a transparent cover. The compartment floor was uniformly divided by lines into 9 squares with 16 holes (openings) of 4 cm diameter. During the 3 minute stay of the rat in the open the following parameters were recorded: number of movements onto the hind paws (vertical movements), the number of passages from one square to another (horizontal movements) and the number of times the rat looked into a hole.

Example 4.5

Results

Assessment of Neurological Deficits Using McGraw Scale

When assessing neurological changes in test rats with cerebral haemorrhage it was found that on the first day after surgical intervention nearly all the animals (90%) showed neurological impairments in the form of atonia, slow movements and limb weakness; these impairments were found in 30% of the pseudo-operated rats. Severe neurological impairments, manifest as circular movements, paresis and limb paralysis, were not observed in the group of pseudo-operated rats, but were found in 50 to 20% of animals with cerebral haemorrhage.

TABLE 12

Effect of biological active blood serum preparation in the form of suppositories (100 mg/kg, rectal) on neurological deficit in rats after suffering cerebral haemorrhage (according to McGraw scale)

| Neurological symptoms | Number of animals with various neurological symptoms, % 1st day after intervention Animal groups | | |
|---|---|---|---|
| | pseudo-operated | after a stroke | Suppositories of biological active blood serum |
| atonia, slow movements | 30 | 90* | 50 |
| limb weakness | 30 | 90* | 43** |
| circular movements | 0 | 40* | 7** |
| paresis 1-4 limbs | 0 | 50* | 36 |
| paralysis 1-4 limbs | 0 | 20 | 0 |

*the accuracy of differences for pseudo-operated rats for $P \leq 0.05$ ($\chi^2$)
*the accuracy of differences for rats with stroke for $P \leq 0.05$ ($\chi^2$)

When two doses of the biological active blood serum preparation in the form of suppositories were administered rectally, the incidence of neurological impairments was reduced. Slight impairments were found in 13-50% of the animals. Strong neurological impairments were found in 7-36% of the rats. When monitoring on the third day a complete disappearance of paresis was observed. The circular movements disappeared on day 10.

Administration of the biological active blood serum preparation in the form of suppositories thus reduces the extent of impaired neurological status in rats one day after a cerebral haemorrhage.

Determination of Muscle Tone in Pull Up Test on Bar.

Determination of muscle tone in rats with cerebral haemorrhage showed that there was impaired muscle tone in a mean 50-56% of rats on the third day after the insult, and 31-27% of the animals on the seventh-fourteenth day.

TABLE 13

Effect of biological active blood serum in the form of suppositories on muscle tone of animals after cerebral haemorrhage in horizontal bar test

| Animal group | Animals that did not pull up on the horizontal bar, in numbers and % | | | | | | | |
|---|---|---|---|---|---|---|---|---|
| | 1st day | | 3rd day | | 7th day | | 14th day | |
| | no. | % | no. | % | no. | % | no. | % |
| Intact (no surgical intervention) | 0/10 | 0 | 0/10 | 0 | 0/10 | 0 | 0/10 | 0 |
| Pseudo-operated | 1/10 | 10 | 2/10 | 20 | 1/10 | 10 | 0/10 | 0 |
| Insult | 10/22 | 50* | 10/18 | 56* | 4/13 | 31 | 3/11 | 27* |
| Insult + suppositories of biological active blood serum | 5/14 | 36 | 4/14 | 29 | 3/14 | 21 | 2/14 | 14** |

*the accuracy of differences for pseudo-operated rats for $P \leq 0.05$ ($\chi^2$)

**the accuracy of differences for rats with stroke for $P \leq 0.05$ ($\chi^2$)

In animals receiving biological active blood serum in the form of suppositories, impaired muscle tone observed on the first and third day was 36% and 29% respectively, on the seventh day 21%, while the figures had fallen to 14% on the fourteenth day and were statistically accurate when compared to the data of insult animals (see Table 13).

Determination of Movement Coordination in Revolving Bar Test

Testing of coordination impairments in rats with cerebral haemorrhage showed that 54-61% of surviving animals had impaired movement coordination on the first-third day, and 38-36% of surviving animals on the seventh-fourteenth day.

A 100 mg/kg dose of the biological active blood serum preparation in the form of suppositories reduced the impairments to movement coordination in rats. This was particularly marked and statistically reliable on the seventh-fourteenth day after the stroke.

TABLE 15

Effect of biological active blood serum suppositories on the execution of the hole reflex

| Animal groups | Latent time before entering the dark compartment after training (hole reflex) 1st day after intervention |
|---|---|
| Intact animals (no surgical intervention) | 7.9 ± 1.3 |
| Pseudo-operated | 11.7 ± 2.1 |
| After insult | 20.4 ± 6.5 |
| biological active blood serum suppositories | 17.8 ± 5.6 |

TABLE 14

Effect of biological active blood serum preparation in form of suppositories on movement coordination of animals after cerebral haemorrhage in revolving bar test

| Animal group | Animals that did not remain on the revolving bar (3 rpm) for 2 minutes, in numbers and % | | | | | | | |
|---|---|---|---|---|---|---|---|---|
| | 1st day | | 3rd day | | 7th day | | 14th day | |
| | no. | % | no. | % | no. | % | no. | % |
| Intact (no surgical intervention) | 0/10 | 0 | 0/10 | 0 | 0/10 | 0 | 0/10 | 0 |
| Pseudo-operated | 2/10 | 20 | 2/10 | 20 | 2/10 | 20 | 1/10 | 10 |
| Insult | 12/22 | 55* | 11/18 | 61* | 5/13 | 38 | 4/11 | 36* |
| Insult + suppositories of biological active blood serum | 6/14 | 43 | 5/14 | 36 | 1/14 | 7** | 1/14 | 7** |

*the accuracy of differences for pseudo-operated rats for $P \leq 0.05$ ($\chi^2$)
**the accuracy of differences for rats with cerebral haemorrhage for $P \leq 0.05$ ($\chi^2$)

Effect of Biological Active Blood Serum Preparation in the Form of Suppositories on Training and Memory Retention and on Execution of Hole Reflex of Animals with Cerebral Haemorrhage The passive avoidance conditioned reflex (PACR) is based on the innate hole reflex of rodents—their instinct to seek out a confined dark space. When they have spent time in an illuminated compartment, the test rats rapidly move over to the dark compartment after a short latent period. The study on the effect of the biological active blood serum preparation in the form of suppositories showed that after training there were no adverse effects on the hole reflex for any of the animals (intact, pseudo-operated, rats with cerebral haemorrhage or rats that had been administered biological active blood serum in the form of suppositories). But although the hole reflex for rats with cerebral haemorrhage was not impaired, the latent time for the reflex to be executed was increased. The biological active blood serum preparation in the form of suppositories did not impair execution of the hole reflex.

Effect of the Biological Active Blood Serum Preparation in the Form of Suppositories on the Impaired Memory Retention of Animals Due to Cerebral Haemorrhage It was found that for the test group that had received the physiological solution rectally during the study (intact group), when the passive avoidance conditioned reflex (PACR) was reproduced 24 hours after training (pain stimulus in the dark compartment), 90% of the animals remembered the electric shock and did not enter the "dangerous" dark compartment over the entire period of observation.

In the group of pseudo-operated animals one day after training, 70% remembered the electric shock in the dark compartment and would no longer enter it.

In the group with the cerebral haemorrhage, 27% of animals no longer entered the dark compartment, i.e. they remembered the electric shock, and in 80% of rats memory was impaired. When the passive avoidance conditioned reflex (PACR) was reproduced on the 14th day after surgical intervention, only 18% of the rats still retained a memory, the figures for intact and pseudo-operated rats after this time were 60% and 70%, respectively. In addition, rats with a stroke had consistently reduced latent time for entering the dark compartment, which also indicates the impaired memory of these animals.

TABLE 16

Effect of biological active blood serum suppositories on reproduction of passive avoidance conditioned reflex (PACR) in rats with post-traumatic intracerebral haematoma

| | Reproduction of the passive avoidance conditioned reflex (PACR) after: | | | |
|---|---|---|---|---|
| | 24 hours after training | | 3 days | |
| Animal groups | Latent time before entering the dark compartment | Number of rats that did not enter the dark compartment, % | Latent time before entering the dark compartment, % | Number of rats that did not enter the dark compartment, % |
| Intact (no surgical intervention) | 162.0 ± 21.0 | 90 | 158.9 ± 17.4 | 80 |
| Pseudo-operated | 139.4 ± 24.2 | 70 | 130.3 ± 19.4 | 70 |
| Insult | 58.4 ± 26.7* | 27* | 83.8 ± 34.5 | 33 |
| Insult + Suppositories of biological active blood serum | 96.2 ± 19.5 | 43 | 113.2 ± 21.7 | 50 |

The biological active blood serum preparation in the form of suppositories administered in a dose of 100 mg/kg 24 hours after training increased by up to 43% the number of animals with retained memory (animals with the cerebral haemorrhage—27%) and increased (by 1.6 times) the latent time before entering the dangerous dark compartment. But these positive effects were not statistically reliable. Three days after the CH (cerebral haemorrhage) intervention and after 3 doses of biological active blood serum in the form of suppositories a positive effect of the preparation on memory was also recorded. However this positive effect was also statistically unreliable.

the 7th day only 23% of animals remembered the negative stimulus and the remaining rats had already entered the dangerous dark compartment after 29 seconds. And after 14 days the passive avoidance conditioned reflex (PACR) was only retained by 18% of the animals (Table 16).

The biological active blood serum preparation in the form of suppositories, which was administered to the rats in a dose of 100 mg/kg (rectal) within 7 days, reestablished memory in the post-cerebral period (the time after the stroke) on the 7th and 14th day after the CH intervention.

Continuation of TABLE 16

| | Reproduction of passive avoidance conditioned reflex (PACR) after: | | | |
|---|---|---|---|---|
| | 7 days | | 14 days | |
| Animal groups | Latent time before entering the dark compartment | Number of rats that did not enter the dark compartment, % | Latent time before entering the dark compartment, % | Number of rats that did not enter the dark compartment, % |
| Intact | 144.1 ± 28.2 | 80 | 150.7 ± 23.4 | 70 |
| Pseudo-operated | 118.3 ± 23.8 | 60 | 121.7 ± 18. | 70 |
| Insult | 28.8 ± 4.6* | 23* | 26.3 ± 9.1* | 18* |
| Insult + suppositories of biological active blood serum | 103.9 ± 19.1** | 50** | 98.4 ± 16.6** | 50** |

*the accuracy of differences of pseudo-operated rats for $P \leq 0.05$ (Student's t test; $\chi^2$)
**the accuracy of differences for rats with stroke for $P \leq 0.05$ (Student's t test; $\chi^2$)

After the 7th and 14th day the intact and pseudo-operated rats remembered the negative situation well and executed the passive avoidance conditioned reflex (PACR). However memory of the pain stimulus in the dark compartment was reliably impaired in rats with cerebral haemorrhage on the 7th-14th day following the intervention. There was more marked impairment of memory compared to the values after the 1st and 3rd day following intervention. For example, after The latent time before entering the dangerous dark compartment also increased by ca. 4 times compared to the insult rats (Table 16).

When administered over 7 days, the biological active blood serum preparation in the form of suppositories thus has the ability to restore memory which has been impaired due to cerebral haemorrhage, using a passive avoidance conditioned reflex (PACR) as a model.

Effect of the Biological Active Blood Serum Preparation in the Form of Suppositories on the Orientation-Exploratory Behaviour of Rats with Cerebral Haemorrhage Investigation of orientation-exploratory behaviour using an "open field" method showed that on the first day after intervention there was a significant reduction in summed values of movement activity and exploratory behaviour in rats with cerebral haemorrhage. The same parameters of rat behaviour were also recorded on the 14th day after cerebral haemorrhage, although the animals were to some extent more active.

When examining the effect of the biological active blood serum preparation 3, 7, and 14 days after the cerebral haemorrhage, the summed values of behaviour had been increased to the level of those in the group of intact animals.

Evaluation of Effect of Biological Active Blood Serum Preparation in the Form of Suppositories on Survival of Rats 45% of the rats died during the surgical intervention or immediately after.

The animals surviving in the first hours after the cerebral haemorrhage were observed over 14 days. As can be seen in Table 18, no fatalities were observed in the group of pseudo-operated rats.

In the group of rats with the cerebral haemorrhage, 18% of the animals died in the first day, and the number rose to 50% by the 14th day. The biological active blood serum preparation in the form of suppositories, which was administered in a dosage of 100 mg/kg rectally daily for 7 days, completely prevented mortality in rats with the cerebral haemorrhage.

TABLE 17

Effect of the biological active blood serum preparation in the form of suppositories on orientation-exploratory behaviour and the movement activity of animals after cerebral haemorrhage using an "open field" method

| Animal group | Horizontal movement | Vertical movement | Investigation of openings | Summed values |
|---|---|---|---|---|
| *1st day after intervention* | | | | |
| Intact | 14.3 ± 2.1 | 7.2 ± 2.3 | 2.9 ± 1.2 | 24.4 ± 5.4 |
| Pseudo-operated | 12.4 ± 2.3 | 4.2 ± 1.3 | 4.0 ± 0.9 | 20.6 ± 4.1 |
| Insult | 8.9 ± 2.2 | 3.7 ± 1.4 | 1.6 ± 0.7 | 14.2 ± 2.5* |
| Insult + biological active blood serum suppositories | 17.6 ± 4.3 | 7.5 ± 3.6 | 3.8 ± 1.4 | 22.9 ± 5.2 |
| *3rd day after intervention* | | | | |
| Intact | 13.4 ± 2.4 | 4.8 ± 1.3 | 3.4 ± 0.9 | 21.6 ± 2.8 |
| Pseudo-operated | 14.1 ± 2.8 | 3.9 ± 1.6 | 3.5 ± 1.1 | 21.5 ± 3.4 |
| Insult | 7.6 ± 2.2* | 3.4 ± 1.2 | 3.3 ± 1.6 | 14.3 ± 3.8* |
| Insult + biological active blood serum suppositories | 16.9 ± 3.7** | 5.6 ± 2.5 | 4.2 ± 1.4 | 26.7 ± 6.5** |
| *7th day after intervention* | | | | |
| Intact | 12.8 ± 2.5 | 5.6 ± 2.1 | 3.0 ± 1.3 | 21.4 ± 4.6 |
| Pseudo-operated | 12.9 ± 2.2 | 3.8 ± 1.5 | 3.1 ± 1.2 | 19.8 ± 4.0 |
| Insult | 7.3 ± 1.4 | 3.4 ± 0.9 | 3.0 ± 0.5 | 13.7 ± 2.7 |
| Insult + biological active blood serum suppositories | 16.4 ± 2.6 | 5.1 ± 1.4 | 5.7 ± 2.0 | 27.2 ± 4.7** |
| *14th day after intervention* | | | | |
| Intact | 13.7 ± 2.5 | 4.8 ± 1.3 | 2.4 ± 0.9 | 20.9 ± 5.3 |
| Pseudo-operated | 13.1 ± 2.1 | 4.3 ± 1.5 | 2.8 ± 1.1 | 20.2 ± 4.8 |
| Insult | 10.2 ± 2.1 | 3.4 ± 0.8 | 3.1 ± 1.4 | 16.7 ± 3.5 |
| Insult + biological active blood serum suppositories | 14.6 ± 1.9 | 5.9 ± 1.4 | 4.8 ± 1.8 | 25.3 ± 4.7** |

*the accuracy of differences of pseudo-operated rats for $P \leq 0.05$ (Student's t-Test)
**the accuracy of differences of rats with stroke for $P \leq 0.05$ (Student's t-Test)

TABLE 18

Effect of biological active blood serum preparation in the form of suppositories on survival of animals after cerebral haemorrhage

| | Number of animals dying in 14 days after cerebral haemorrhage | | | | | | | |
|---|---|---|---|---|---|---|---|---|
| | 1st day | | 3rd day | | 7th day | | 14th day | |
| Animal group | no. | % | no. | % | no. | % | no. | % |
| Pseudo-operated | 0/10 | 0 | 0/10 | 0 | 0/10 | 0 | 1/10 | 10 |
| Insult | 5/27 | 18* | 4/22 | 18* | 5/18 | 28* | 2/13 | 15* |
| Insult + suppositories of biological active blood serum | 0/14 | 0** | 0/14 | 0* | 0/14 | 0** | 0/14 | 0** |

*the accuracy of differences of pseudo-operated rats for $P \leq 0.05$ ($\chi^2$)
**the accuracy of differences of rats with stroke for $P \leq 0.05$ ($\chi^2$)

Example 4.6

Summary of the Results of Examples 4.1 to 4.5

The above described investigations showed that the rats with cerebral haemorrhage (post-traumatic intracerebral haematoma) had a pronounced neurological deficit, impairment of movement coordination, impairment of training processes and memory, and higher numbers of animal fatalities compared with the pseudo-operated animals. The intensification of pathological symptoms was recorded up to the 14th day after the induced cerebral haemorrhage.

After being administered to the animals rectally in a dosage of 100 mg/kg 5 hours after intervention, and then daily for 7 days, the biological active blood serum preparation in the form of suppositories resulted in significant improvements to post-cerebral impairments. The preparation improved parameters indicating neurological deficit according to the McGraw scale already one day after the stroke, and when used similarly to a course of treatment, it increased muscle tone and improved movement coordination by the 7th and 14th day following the stroke. When administered repeatedly the biological active blood serum preparation in the form of suppositories improved memory impaired due to the stroke and improved reproduction of the passive avoidance conditioned reflex on the 7th and 14th day after the insult. A particularly marked effect of the biological active blood serum preparation in the form of suppositories was its ability to completely prevent mortality in animals with the cerebral haemorrhage.

The biological active blood serum preparation (100 mg/kg, rectal) thus shows cerebroprotective activity in rats when administered over 7 days, using a model of cerebral haemorrhage (post-traumatic intracerebral haematoma). This effect is manifest as an improvement of neurological status, general behaviour, cognitive functions and a reduction in animal mortality rates.

The invention claimed is:

1. A method for treating stroke wherein said method comprises administering, to a subject in need of such treatment, a biologically active blood serum made by a method comprising the steps of:
   a) electrostimulation of a non-human animal,
   b) withdrawal of blood from said animal,
   c) isolation of serum from said blood, and
   d) gamma irradiation of said serum.

2. The method according to claim 1, wherein the non-human animal is selected from the group consisting of mammals and birds.

3. The method according to claim 2, wherein the bird is selected from the group consisting of chicken, duck, goose, ostrich, and quail.

4. The method according to claim 1, wherein in step a) the head, the neck, the body and/or one or more limbs is electro stimulated.

5. The method according to claim 1, wherein the electro stimulation is carried out for a time period of between 1 and 60 seconds.

6. The method according to claim 1, wherein the electro stimulation is carried out with a voltage in the range of between 50 V and 150 V.

7. The method according to claim 1, wherein the electro stimulation is carried out with a current in the range of between 0.01 A and 0.4 A.

8. The method according to claim 1, wherein the electro stimulation is carried out with a frequency in the range of between 10 and 200 Hz.

9. The method according to claim 1, wherein said gamma irradiation is administered with an adsorbed radiation dose of between 15 to 35 kGy.

10. The method according to claim 1, wherein the source of the gamma radiation is selected from the group consisting of $^{60}$Co, $^{137}$Cs, $^{37}$Cu, $^{37}$Ga, $^{111}$In, $^{192}$Ir, $^{99m}$Tc and $^{170}$Tm.

11. The method according to claim 1, wherein the method further comprises the step of incubating said blood prior to step c).

12. The method according to claim 1, wherein the method further comprises the step of lyophilization of said serum prior to step d).

13. The method according to claim 1, wherein said blood is arterial and/or venous blood.

14. The method according to claim 1, wherein said blood serum further comprises one or more pharmaceutically acceptable diluents; carriers; excipients, including fillers, binders, lubricants, glidants, disintegrants, adsorbents; and/or preservatives.

15. The method according to claim 1, wherein the biologically active blood serum is formulated as a syrup, an infusion or injection solution, a tablet, a capsule, a capslet, a lozenge, a liposome, a suppository, a plaster, a band-aid, a retard capsule, a powder, or a slow release formulation.

16. The method according to claim 1, wherein the biologically active blood serum is administered to a subject in need of treatment in an amount ranging from 1 to 500 mg/kg body weight.

17. The method according to claim 1, wherein the biologically active blood serum is administered 24 hours after a stroke.

18. The method according to claim 1, wherein administration is continued for at least 1 week after the stroke.

19. The method according to claim 1, wherein said stroke is selected from an ischemic, thrombotic, embolic, or transient stroke.

20. The method, according to claim 1, wherein the animal is a chicken.

21. The method, according to claim 1, wherein the administration of the biologically active blood serum to the subject results in improved locomotive activity of the subject.

22. The method, according to claim 1, wherein the administration of the biologically active blood serum to the subject results in reduced mortality.

23. The method, according to claim 1, wherein the administration of the biologically active blood serum to the subject results in improved memory of the subject.

24. The method, according to claim 1, wherein administration of the biologically active blood serum to the subject results in improved cognitive function of the subject.

25. The method, according to claim 1, wherein the biologically active blood serum is not administered directly to the brain of the subject.

26. The method, according to claim 25, wherein the blood serum is administered by a route selected from the group consisting of oral, rectal, intragastrical, intravenous, intramuscular, intranasal, intradermal, and subcutaneous.

* * * * *

UNITED STATES PATENT AND TRADEMARK OFFICE
CERTIFICATE OF CORRECTION

PATENT NO. : 7,744,926 B2 Page 1 of 1
APPLICATION NO. : 11/404971
DATED : June 29, 2010
INVENTOR(S) : Vitali A. Shestakov It is certified that error appears in the above-identified patent and that said Letters Patent is hereby corrected as shown below:

Column 38:
Line 44, "$^{37}$Cu, $^{37}$Ga" should read --$^{67}$Cu, $^{67}$Ga--

Signed and Sealed this

Second Day of November, 2010

David J. Kappos
*Director of the United States Patent and Trademark Office*